US010711249B2

(12) United States Patent
Osafune et al.

(10) Patent No.: US 10,711,249 B2
(45) Date of Patent: Jul. 14, 2020

(54) METHOD FOR INDUCING HEPATOCYTES

(71) Applicant: KYOTO UNIVERSITY, Kyoto-shi, Kyoto (JP)

(72) Inventors: Kenji Osafune, Kyoto (JP); Maki Kotaka, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 171 days.

(21) Appl. No.: 15/539,042

(22) PCT Filed: Dec. 25, 2015

(86) PCT No.: PCT/JP2015/086260
§ 371 (c)(1),
(2) Date: Nov. 22, 2017

(87) PCT Pub. No.: WO2016/104717
PCT Pub. Date: Jun. 30, 2016

(65) Prior Publication Data
US 2018/0119095 A1    May 3, 2018

(30) Foreign Application Priority Data
Dec. 26, 2014  (JP) ................ 2014-265062

(51) Int. Cl.
*C12N 5/071*   (2010.01)
*G01N 33/50*   (2006.01)

(52) U.S. Cl.
CPC ......... *C12N 5/067* (2013.01); *G01N 33/5067* (2013.01); *C12N 2500/30* (2013.01); *C12N 2500/62* (2013.01); *C12N 2501/12* (2013.01); *C12N 2501/16* (2013.01); *C12N 2501/237* (2013.01); *C12N 2501/31* (2013.01); *C12N 2501/39* (2013.01); *C12N 2501/727* (2013.01); *C12N 2501/73* (2013.01); *C12N 2501/80* (2013.01); *C12N 2501/999* (2013.01); *C12N 2506/02* (2013.01); *C12N 2506/45* (2013.01)

(58) Field of Classification Search
CPC .................................................... C12N 5/067
See application file for complete search history.

(56) References Cited

U.S. PATENT DOCUMENTS

| | | | |
|---|---|---|---|
| 8,048,999 B2 | 11/2011 | Yamanaka et al. | |
| 8,791,248 B2 | 7/2014 | Yamanaka et al. | |
| 2003/0087919 A1 | 5/2003 | Nagarathnam et al. | |
| 2003/0125344 A1 | 7/2003 | Nagarathnam et al. | |
| 2004/0002507 A1 | 1/2004 | Nagarathnam et al. | |
| 2004/0002508 A1 | 1/2004 | Nagarathnam et al. | |
| 2004/0014755 A1 | 1/2004 | Nagarathnam et al. | |
| 2005/0119463 A1 | 6/2005 | Mukaidani et al. | |
| 2005/0192304 A1 | 9/2005 | Nagarathnam et al. | |
| 2005/0209261 A1 | 9/2005 | Nagarathnam et al. | |
| 2014/0234341 A1 | 8/2014 | Tsubouchi et al. | |

FOREIGN PATENT DOCUMENTS

| | | | | |
|---|---|---|---|---|
| EP | 2 096 169 A1 | 9/2009 | | |
| JP | 2010-029211 A | 2/2010 | | |
| JP | 2013-252081 A | 12/2013 | | |
| JP | WO 2013/183571 A1 | * 12/2013 | ............... | C12N 5/10 |
| WO | 1999/035246 A1 | 7/1999 | | |
| WO | 2001/081549 A2 | 11/2001 | | |
| WO | 2002/076976 A2 | 10/2002 | | |
| WO | WO 2002/088332 | 11/2002 | | |
| WO | 2003/059913 A1 | 7/2003 | | |
| WO | 2003/062225 A1 | 7/2003 | | |
| WO | 2003/062227 A1 | 7/2003 | | |
| WO | 2003/080670 A1 | 10/2003 | | |
| WO | 2004/039796 A1 | 5/2004 | | |
| WO | 2006/126574 A1 | 11/2006 | | |
| WO | 2007/050043 A2 | 5/2007 | | |
| WO | 2007/069666 A1 | 6/2007 | | |
| WO | WO 2008/094597 | 8/2008 | | |
| WO | 2008/118820 A2 | 10/2008 | | |
| WO | 2009/007852 A2 | 1/2009 | | |
| WO | 2009/032194 A1 | 3/2009 | | |
| WO | 2009/057831 A1 | 5/2009 | | |
| WO | 2009/058413 A1 | 5/2009 | | |
| WO | 2009/075119 A1 | 6/2009 | | |
| WO | 2009/079007 A1 | 6/2009 | | |
| WO | 2009/091659 A2 | 7/2009 | | |

(Continued)

OTHER PUBLICATIONS

Hannan et al. (2013, Nat. Protoc., vol. 8(2), pp. 430-437) (Year: 2013).*
Kondo et al. (epub Dec. 2013, Drug Metab. Pharmacokinet., vol. 29(3), pp. 237-243) (Year: 2013).*
Konstandi et al. (2013, PLOS ONE, vol. 8(8), pp. 1-12) (Year: 2013).*
Kallas et al. (Feb. 2014, Stem Cells Int., Article ID 298163, pp. 1-12). (Year: 2014).*
Eminli et al. (2008) "Reprogramming of neural progenitor cells into induced pluripotent stem cells in the absence of exogenous Sox2 expression," Stem Cells. 26:2467-2474.
Feng et al. (2009) "Reprogramming of fibroblasts into induced pluripotent stem cells with orphan nuclear receptor Esrrb," Nat. Cell. Biol. 11:197-203.

(Continued)

*Primary Examiner* — Thaian N. Ton
*Assistant Examiner* — David A. Montanari
(74) *Attorney, Agent, or Firm* — Lathrop GPM LLP; James H. Velema, Esq.; Judith Stone-Hulslander

(57) ABSTRACT

A method for producing hepatocytes from hepatoblasts is provided. The method includes the step of culturing the hepatoblasts in a medium containing a compound selected from the group consisting of pregnenolone and an adrenergic agonist. The hepatoblasts can be obtained by culturing endodermal cells in a medium containing DMSO, and the endodermal cells can be obtained by culturing pluripotent stem cells in a medium containing Activin A and a GSK-3β inhibitor. Accordingly, a method for producing hepatocytes from pluripotent stem cells is also provided by employing the method of the present invention.

9 Claims, 14 Drawing Sheets

Specification includes a Sequence Listing.

(56) References Cited

FOREIGN PATENT DOCUMENTS

| WO | 2009/101084 A1 | 8/2009 |
|---|---|---|
| WO | 2009/101407 A2 | 8/2009 |
| WO | 2009/102983 A2 | 8/2009 |
| WO | 2009/114949 A1 | 9/2009 |
| WO | 2009/117439 A2 | 9/2009 |
| WO | 2009/126250 A2 | 10/2009 |
| WO | 2009/126251 A2 | 10/2009 |
| WO | 2009/126655 A2 | 10/2009 |
| WO | 2009/157593 A1 | 12/2009 |
| WO | 2010/009015 A2 | 1/2010 |
| WO | 2010/033906 A2 | 3/2010 |
| WO | 2010/033920 A2 | 3/2010 |
| WO | 2010/042800 A1 | 4/2010 |
| WO | 2010/050626 A1 | 5/2010 |
| WO | 2010/056831 A2 | 5/2010 |
| WO | 2010/068955 A2 | 6/2010 |
| WO | 2010/098419 A1 | 9/2010 |
| WO | 2010/102267 A2 | 9/2010 |
| WO | 2010/111409 A2 | 9/2010 |
| WO | 2010/111422 A2 | 9/2010 |
| WO | 2010/115050 A2 | 10/2010 |
| WO | 2010/124290 A2 | 10/2010 |
| WO | 2010/147395 A2 | 12/2010 |
| WO | 2010/147612 A1 | 12/2010 |
| WO | 2012/144535 A1 | 10/2012 |
| WO | 2013/183571 A1 | 12/2013 |
| WO | 2014/083132 A1 | 6/2014 |

OTHER PUBLICATIONS

Han et al. (2010) "Tbx3 improves the germ-line competency of induced pluripotent stem cells," Nature. 463:1096-1100.

Hay et al. (2008) "Efficient differentiation of hepatocytes from human embryonic stem cells exhibiting markers recapitulating liver development in vivo," Stem Cells. 26:894-902.

Heng et al. (2010) "The nuclear receptor Nr5a2 can replace Oct4 in the reprogramming of murine somatic cells to pluripotent cells," Cell Stem Cell. 6:167-174.

Huangfu et al. (2008) "Induction of pluripotent stem cells by defined factors is greatly improved by small-molecule compounds" Nat Biotechnol. 26:795-797.

Huangfu et al. (2008) "Induction of pluripotent stem cells from primary human fibroblasts with only Oct4 and Sox2," Nat. Biotechnol. 26:1269-1275.

Ichida et al. (2009) "A small-molecule inhibitor of tgf-Beta signaling replaces sox2 in reprogramming by inducing nanog," Cell Stem Cell. 5:491-503.

Ishizaki et al. (2000) "Pharmacological properties of Y-27632, a specific inhibitor of rho-associated kinases," Mol. Pharmacol. 57:976-983.

Judson et al. (2009) "Embryonic stem cell-specific microRNAs promote induced pluripotency," Nat. Biotech. 27:459-461.

Kajiwara et al. (2012) "Donor-dependent variations in hepatic differentiation from human-induced pluripotent stem cells," Proc. Natl. Acad. Sci. USA. 109:12538-12543.

Kim et al. (2009) "Direct reprogramming of human neural stem cells by OCT4," Nature. 461:649-643.

Lyssiotis et al. (2009) "Reprogramming of murine fibroblasts to induced pluripotent stem cells with chemical complementation of Klf4," Proc. Natl. Acad. Sci. USA. 106:8912-8917.

Maekawa et al. (2011) "Direct reprogramming of somatic cells is promoted by maternal transcription factor Glis1," Nature. 474:225-229.

Mali et al. (2010) "Butyrate greatly enhances derivation of human induced pluripotent stem cells by promoting epigenetic remodeling and the expression of pluripotency-associated genes," Stem Cells. 28:713-720.

Marson et al. (2008) "Wnt signaling promotes reprogramming of somatic cells to pluripotency," Cell Stem Cell. 3:132-135.

Nakajima et al. (2003) "Effect of Wf-536, a novel ROCK inhibitor, against metastasis of B16 melanoma," Cancer Chemother. Pharmacol. 52(4):319-324.

Narumiya et al. (2000) "Use and properties of ROCK-specific inhibitor Y-27632," Methods Enzymol. 32:273-284.

Okita et al. (Feb. 25, 2013) "An Efficient Nonviral Method to Generate Integration-Free Human-Induced Pluripotent Stem Cells from Cord Blood and Peripheral Blood Cells," Stem Cells. 31:458-466.

Sasaki et al. (2002) "The novel and specific Rho-kinase inhibitor (S)-(+)-2-methyl-1-[(4-methyl-5-isoquinoline)sulfonyl]-homopiperazine as a probing molecule for Rho-kinase-involved pathway," Pharmacol. Ther. 93:225-232.

Shi et al. (2008) "A Combined Chemical and Genetic Approach for the Generation of Induced Pluripotent Stem Cells," Cell Stem Cell. 2:525-528.

Shi et al. (2008) "Induction of pluripotent stem cells from mouse embryonic fibroblasts by Oct4 and Klf4 with small-molecule compounds," Cell Stem Cell. 3:568-574.

Takahashi et al. (2007) "Induction of pluripotent stem cells from adult human fibroblasts by defined factors," Cell. 131:861-872.

Takayama et al. (Oct. 3, 2013) "Long-Term Self-Renewal of Human ES/iPS-Derived Hepatoblast-like Cells on Human Laminin 111-Coated Dishes," Stem Cell Reports. 1:322-335.

Uehata et al. (1997) "Calcium sensitization of smooth muscle mediated by a Rho-associated protein kinase in hypertension," Nature. 389:990-994.

Ying et al. (2008) "The ground state of embryonic stem cell self-renewal," Nature. 453:519-523.

Zhao et al. (2008) "Two supporting factors greatly improve the efficiency of human iPSC generation," Cell Stem Cell. 3:475-479.

International Preliminary Report on Patentability corresponding to International Patent Application No. PCT/JP2015/086260, dated Jun. 27, 2017—English translation provided only.

Konstandi et al. (Aug. 14, 2013) "Role of PPARα and HNF4α in stress-mediated alterations in lipid homeostasis," PLoS One. 8(8):e70675. pp. 1-12.

Kubota et al. (Nov. 25, 2014) "Role of pregnane X receptor and aryl hydrocarbon receptor in transcriptional regulation of pxr, CYP2, and CYP3 genes in developing zebrafish," Toxicol. Sci. 143(2):398-407.

Miyamoto et al. (2005) "Expression of cytochrome P450 enzymes in hepatic organoid reconstructed by rat small hepatocytes," J. Gasteroenterol. Hepatol. 20:865-872.

Zaret (2002) "Regulatory phases of early liver development: paradigms of organogenesis," Nat. Rev. Genet. 3:499-512.

International Search Report with Written Opinion corresponding to International Patent Application No. PCT/JP2015/086260, dated Apr. 5, 2016.

De Juan et al. (2012) "Regulation of Albumin Expression in Fetal Rat Hepatocytes Cultured Under Proliferative Conditions: Role of Epidermal Growth Factor and Hormones," Journal of Cellular Physiology, 152-95-101, 7 pp.

Mansuroglu et al. (2009) "Hepatoblast and mesenchymal cell-specific gene-expression in fetal rat liver and in cultured fetal rat liver cells," Histochem Cell Biol, 132, 9 pp.

Andersson (1983) "β-Adrenergic Induction of Tyrosine Aminotransferase in Organ Culture of Fetal Rat and Fetal Human Liver," Endocrinology, vol. 112, No. 2, 4 pp.

Pfandler et al. (2004) "Small hepatocytes in culture develop polarized transporter expression and differentiation," Journal of Cell Science, 117, 11 pp.

Kissling et al. (1997) "$\alpha_1$-Adrenoceptor-mediated negative inotropy of adrenaline in rat myocardium," Journal of Physiology, 499.1, 11 pp.

Docherty (2008) "Pharmacology of stimulants prohibited by the World Anti-Doping Agency (WADA," British Journal of Pharmacology, 154, 17 pp.

Wobus et al. (2011) "Present state and future perspectives of using pluripotent stem cells in toxicology research," Arch Toxicol, 85, 39 pp.

(56) References Cited

OTHER PUBLICATIONS

Chikada et al. (2015) "The basic helix-loop-helix transcription factor, $Mist_1$, induces maturation of mouse fetal hepatoblasts," Scientific Reports, 5:14989, 12 pp.

Fabregat et al. (1994) "Noradrenergic Modulation of Albumin Expression in Growth-Stimulated Adult Rat Hepatocytes in Primary Culture," J. Cell. Phys., 158, 5 pp.

Konstandi et al. (2013) "Role of PPARa and HNF4a in Stress-Mediated Alterations in Lipid Homeostasis," PLOS ONE, vol. 8, Issue 8, 12 pp.

Kotaka et al. (2017) "Adrenergic receptor agonists induce the differentiation of pluripotent stem cell-derived hepatoblasts into hepatocyte-like cells," Scientific Reports, 7, 16734, 13 pp.

Leoni et al. (1993) "Intracellular Signalling of Epinephrine in Rat Hepatocytes During Fetal Development and Hepatic Regeneration," Bioscience Reports, vol. 13, No. 1, 8 pp.

Mitaka (1998) "The current status of primary hepatocyte culture," Int. J. Exp. Path., 79, 17 pp.

Miyamoto et al. (2005) "Expression of cytochrome P450 enzymes in hepatic organoid reconstructed by rat small hepatocytes," J. Gastroenterology & Hepatology, 20, 8 pp.

Turner et al. (2011) "Human Hepatic Stem Cell and Maturational Liver Lineage Biology," Hepatology, Mar. 2011, 11 pp.

Zaret (2002) "Regulatory phases of early liver development: paradigms of organogenesis," Nature Reviews, Genetics, vol. 3, 14 pp.

Japanese Patent Application No. 2016-566521, Office Action dated Oct. 29, 2019, 19 pages.

\* cited by examiner

ALBUMIN(GFP)+

PCA(PC1 vs PC2 vs PC3)

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
cgctattagt tcgttacacc a                                             21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tttacaacat ttgctgccca                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ccaccaagaa ctgcttagcc                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cagctccaaa gaggtccaag                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aagacccctt tgtggaaaac                                               20

<210> SEQ ID NO 6
<211> LENGTH: 20
<212> TYPE: DNA
<213> ORGANISM: Artificial Sequence
```

```
<220> FEATURE:
<223> OTHER INFORMATION: primer

<400> SEQUENCE: 6
cgaggcgact ttctttcatc                                           20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ctctctgttt ccaaaagata cc                                        22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tgaagattat tgactgggct g                                         21

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
agatttaatc cattagatcc attcg                                     25

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aggcgacctt cttttatctg                                           20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gaacaccaag aatcgatgga ca                                        22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
tcagcaggag aaggagagca ta                                        22
```

-continued

```
<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
atctctgtta tggggcgttg                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgatgaccac tcggatgaaa                                              20
```

METHOD FOR INDUCING HEPATOCYTES

RELATED APPLICATIONS

This application is a 35 U.S.C. § 371 filing of International Patent Application No. PCT/JP2015/086260, filed Dec. 25, 2015, which claims priority to Japanese Patent Application No. 2014-265062, filed Dec. 26, 2014, each of which is incorporated herein by reference in its entirety.

TECHNICAL FIELD

The present invention relates to a method for inducing differentiation of pluripotent stem cells into hepatocytes.

BACKGROUND ART

Many patients die of liver failure such as chronic liver failure including liver cirrhosis and acute liver failure every year. As a radical treatment for these diseases, liver transplantation is presently carried out. Since the liver transplantation is a highly invasive treatment, a safer treatment, hepatocyte transplantation, has been proposed. However, the hepatocyte transplantation requires a large amount of cells at a time. Because of this, deficiency in donors is concerned.

Development of pharmaceutical candidate compounds is terminated mainly due to "hepatotoxicity". Thus, in development of pharmaceutical products, the toxicity is evaluated by using a human hepatocyte primary culture, in vitro. However, it is difficult to stably supply the hepatocyte primary culture with lot-to-lot uniformity and thus stable inspection results are not obtained.

Then, for transplantation and search for pharmaceutical products, producing hepatocytes from pluripotent stem cells such as embryonic stem cells (ES cells) or induced pluripotent stem cells (iPS cells) has attracted attention. Up to present, a number of methods of producing hepatocytes from pluripotent stem cells have been reported (Patent Literature 1, Non Patent Literature 1, Non Patent Literature 2, Non Patent Literature 3). In the methods reported, proteins such as HGF and oncostatin M are employed for efficient maturation into hepatocytes. However, if such a protein is used, cost for cell induction increases and efficiency varies depending upon lot-to-lot variation of the protein. We occasionally come across such problems.

CITATION LIST

Patent Literature

Patent Literature 1: WO2001/081549

Non Patent Literatures

Non Patent Literature 1: Takayama K, et al, Stem Cell Reports. 1: 322-335, 2013.
Non Patent Literature 2: Kajiwara M, et al, Proc Natl Acad Sci USA. 109: 12538-12543, 2012
Non Patent Literature 3: Hay D C, et al, Stem Cells. 26: 894-902, 2008.

The Patent Literature and Non Patent Document are herein incorporated by reference.

SUMMARY OF INVENTION

Problems to be Solved by the Invention

An object of this application is to provide a method for inducing differentiation of hepatoblasts into hepatocytes in vitro. Another object of this application is to provide a method of inducing hepatoblasts from endodermal cells and then inducing differentiation of the hepatoblasts into hepatocytes in vitro. Specifically, this application is directed to an in vitro method including inducing endodermal cells from pluripotent stem cells, then inducing hepatoblasts from the endodermal cells and further inducing differentiation of the hepatoblasts into hepatocytes.

Means for Solving the Problems

The present inventors conducted intensive studies with a view to attaining the above objects. As a result, the inventors for the first time found that hepatoblasts are induced by culturing endodermal cells in a medium containing dimethylsulfoxide (hereinafter referred to as DMSO) and hepatocytes are induced and differentiated by culturing the hepatoblasts in a medium containing pregnenolone or an adrenergic agonist. The present invention was accomplished based on the finding.

More specifically, the present invention has the following characteristics:

[1] A method for producing hepatocytes, including the step of culturing hepatoblasts in a medium containing pregnenolone or an adrenergic agonist, wherein the hepatoblasts are AFP-positive.

[2] The method according to [1], wherein the adrenergic agonist is a compound selected from the group consisting of adrenaline, noradrenaline, etilefrine, naphazoline, phenylephrine, methoxamine and midodrine.

[3] The method according to [2], wherein the adrenergic agonist is a compound selected from the group consisting of etilefrine, phenylephrine and methoxamine.

[4] The method according to any one of [1] to [3], wherein the hepatoblasts are cells produced by a method including the step of culturing endodermal cells in a medium containing DMSO, and the endodermal cells are SOX17-positive cells.

[5] The method according to [4], wherein the endodermal cells are cells produced by a method including the step of culturing pluripotent stem cells in a medium containing Activin A and a GSK-3β inhibitor.

[6] The method according to [5], wherein the step of producing endodermal cells from the pluripotent stem cells further includes a culture step in a medium containing Activin A, a GSK-3β inhibitor and an HDAC inhibitor.

[7] The method according to [6], wherein the GSK3β inhibitor is CHIR99021; and the HDAC inhibitor is NaB (sodium butyrate).

[8] The method according to any one of [5] to [7], wherein the pluripotent stem cells are iPS cells.

[9] The method according to [8], wherein the iPS cells are human iPS cells.

[10] The method according to any one of [5] to [7], wherein the pluripotent stem cells are ES cells.

[11] A method for producing hepatocytes from pluripotent stem cells, including the following steps (i) to (iii):
(i) culturing pluripotent stem cells in a medium containing Activin A and a GSK-3β inhibitor,
(ii) culturing the cells obtained in step (i) in a medium containing DMSO, and
(iii) culturing the cells obtained in step (ii) in a medium containing an agent selected from the group consisting of pregnenolone and an adrenergic agonist.

[12] The method according to [11], wherein the adrenergic agonist is a compound selected from the group consisting of adrenaline, noradrenaline, etilefrine, naphazoline, phenylephrine, methoxamine and midodrine.

[13] The method according to [12], wherein the adrenergic agonist is a compound selected from the group consisting of etilefrine, phenylephrine and methoxamine.

[14] The method according to [13], wherein the step (i) further includes a culture step in a medium containing Activin A, a GSK-3β inhibitor and an HDAC inhibitor.

[15] The method according to [14], wherein the GSK3β inhibitor is CHIR99021 and the HDAC inhibitor is NaB (sodium butyrate).

[16] The method according to any one of [11] to [15], wherein the pluripotent stem cells are iPS cells.

[17] The method according to [16], wherein the iPS cells are human iPS cells.

[18] The method according to any one of [11] to [15], wherein the pluripotent stem cells are ES cells.

[19] A method for detecting a metabolite of a test substance, including the step of bringing the hepatocytes produced by the method according to any one of [1] to [17] and the test substance into contact with each other.

[20] A method for detecting induction of a drug metabolizing enzyme of a test substance, including the step of bringing the hepatocytes produced by the method according to any one of [1] to [17] and the test substance into contact with each other.

Advantageous Effects of Invention

It has been made possible to induce hepatocytes from endodermal cells by using a relatively low-molecular compound. The endodermal cells can be induced from pluripotent stem cells. Owing to the method of the present invention, it has become possible to provide hepatocytes having stable properties. The method of inducing hepatocyte according to the present invention is completely carried out in vitro. The hepatocytes produced by the method of the present invention can be used as a regenerative medicine for liver diseases such as liver failure and in the evaluation of e.g., effectiveness and safeness of drugs.

DESCRIPTION OF EMBODIMENTS

Figure 1:
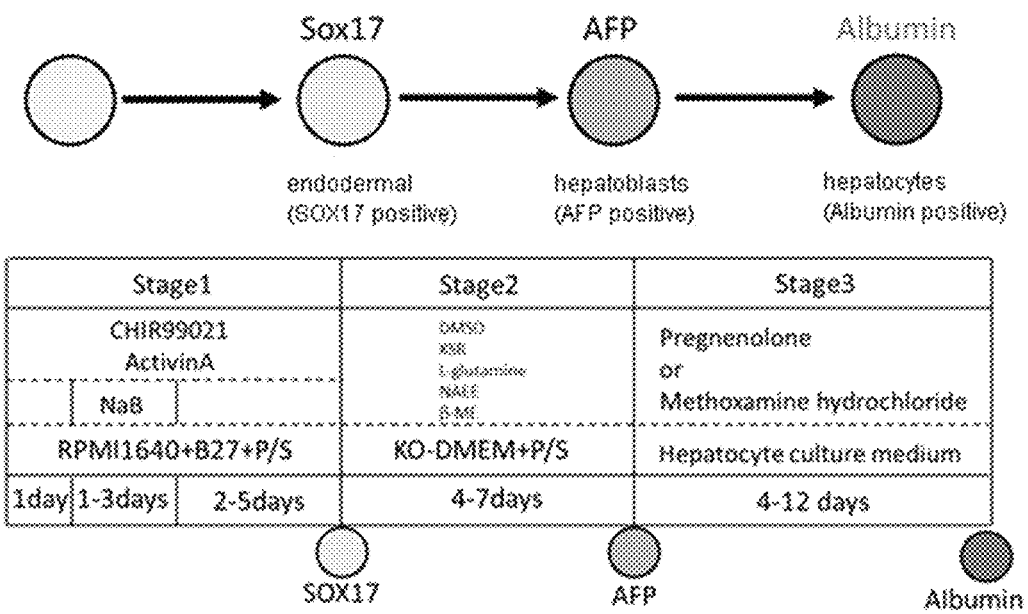
FIG. 1 schematically show the induction of hepatocytes from human iPS cells.

The present invention will be more specifically described below.

The present invention provides a method for producing hepatocytes including the step of culturing hepatoblasts in a medium containing an agent selected from the group consisting of pregnenolone and an adrenergic agonist.

In an embodiment of the present invention, the hepatocytes are defined as the cells expressing albumin mRNA.

In another embodiment of the present invention, the hepatocytes may be defined as the cells characterized by having functions known as functions of hepatocytes, such as accumulation of glycogen, uptake of a low density lipoprotein (LDL), secretion of albumin, ammonia metabolism and urea synthesis, cytochrome P450 activity, fat metabolism and metabolization of drugs, alone or in combination. The determination of hepatocytes can be verified based on expression of proteins involved in these functions. In the present invention, hepatocytes may be provided as a cell population containing hepatocytes and cells other than hepatocytes or as a purified cell population, and preferably as a cell population containing 20% or more, 30% or more, 40% or more or 50% or more of hepatocytes.

In the present invention, hepatoblasts are cells having an ability to differentiate into hepatocytes and biliary epithelial cells, and cells having at least one marker gene selected from the group consisting of AFP, Dlk, E-cadherin, Liv2, CD13 and CD133, being positive, and preferably AFP-positive cells.

In the present invention, hepatocytes are produced from hepatoblasts by culturing hepatoblasts in a medium containing an agent selected from the group consisting of pregnenolone and an adrenergic agonist.

In the method of this application, hepatoblasts may be provided as a cell population containing hepatoblasts and cells other than hepatoblasts, or may be as a purified cell population, and is preferably a cell population containing 30% or more, 40% or more, 50% or more, 60% or more, 70% or more, 80% or more, 90% or more or 100% of hepatoblasts. As a method for purifying hepatoblasts, for example, a method including staining hepatoblasts with an antibody against a gene maker, such as AFP, Dlk, E-cadherin, Liv2, CD13 or CD133, and concentrating the stained cells by use of a flow cytometer (FACS) or a magnetic cell separation device (MACS), is mentioned. More preferably a method of using an antibody against Dlk, E-cadherin, Liv2, CD13 or CD133 is mentioned. As the antibody against Dlk, E-cadherin, Liv2, CD13 or CD133, a commercially available antibody can be appropriately used.

When a culture of a cell population containing hepatoblasts is provided in a state of being attached to a culture dish, the method of this application can be carried out by replacing the medium of the culture containing hepatoblasts with a medium containing an agent selected from the group consisting of pregnenolone and an adrenergic agonist, while maintaining the state of adhesion. In contrast, when the culture of a cell population containing hepatoblasts is provided in a suspension state in a medium, the medium for a cell population culture containing hepatoblasts is replaced with a medium containing an agent selected from the group consisting of pregnenolone and an adrenergic agonist and then a suspension culture is carried out. Alternatively, the culture of a cell population containing hepatoblasts may be subjected to adhesion culture carried out by use of a coated culture dish and in a medium containing an agent selected from the group consisting of pregnenolone and an adrenergic agonist. Preferably, the step of producing hepatocytes from hepatoblasts is carried out by adhesion culture.

When hepatoblasts are provided in the form of cell mass in which cells mutually adhere, the hepatoblasts may be substantially separated (dissociated) into single cells by some sort of means and then cultured. As the separation method, for example, mechanical separation and separation using a separation solution having a protease activity and a collagenase activity (for example, solution containing trypsin and collagenase, i.e., Accutase™ and Accumax™ (Innovative Cell Technologies, Inc.)) or a separation solution having a collagenase activity alone may be mentioned.

When adhesion culture is employed for producing hepatocytes from hepatoblasts, the culture may be carried out in a coated culture dish. Examples of coating agents may include matrigel (BD Biosciences), Synthemax (Corning), collagen, gelatin, laminin (preferably, e.g., laminin 111, 411 or 511), heparan sulfate proteoglycan, entactin, or a fragment thereof and a combination thereof. When the cell population containing hepatoblasts is provided as a culture attached to a dish, it is preferable to induce hepatocytes by replacing the medium alone while maintaining the conditions in which the hepatoblasts were obtained.

In the present invention, the phrase "hepatoblasts are cultured in a suspension condition in producing hepatocytes" means that the hepatoblasts are cultured in a culture dish so as not to be in contact with the dish. Although the conditions of the suspension culture are not particularly limited, the culture can be carried out by using a culture dish to which an artificial treatment (for example, treatment such as coating with an extracellular matrix) for improving the adhesion between the cells and the culture dish is not applied or a culture dish artificially treated so as to suppress adhesion (for example, coating treatment with polyhydroxyethyl methacrylate (poly-HEMA)).

The medium to be used in the step of producing hepatocytes from hepatoblasts according to the present invention can be prepared by appropriately adding an agent selected from the group consisting of pregnenolone and an adrenergic agonist to a medium for culturing hepatocytes. As the medium for culturing hepatocytes, for example, IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, HBM™ Basal Medium, HCM™ SingleQuots™ Kit, HMM™ Basal Medium or HMM™ SingleQuots™ Kit (Lonza); Hepatocyte Growth Medium or Hepatocyte Maintenance Medium (PromoCell) or Hepatocyte Medium (Sigma-Aldrich) and a mixed medium of these are included. These basic mediums may or may not contain serum (for example, fetal bovine serum (FBS)). A serum-free medium may contain, if necessary, one or more such as serum replacements such as albumin, transferrin, KnockOut Serum Replacement (KSR) (serum substitute for culturing ES cells) (Invitrogen), N2 supplement (Invitrogen), B27 supplement (Invitrogen), a fatty acid, insulin, sodium selenite, a collagen precursor, a trace element, 2-mercaptoethanol and 3'-thiol glycerol. The medium may also contain one or more substances such as a lipid, an amino acid, L-glutamine, GlutaMAX (Invitrogen), a nonessential amino acid (NEAA), a vitamin (e.g., nicotinamide, ascorbic acid), a growth factor, an antibiotic, an antioxidant, pyruvic acid, a buffer, an inorganic salt, glucagon, hydrocortisone, EGF (Epidermal growth factor), dexamethasone and equivalents to these.

In the present invention, as pregnenolone, a commercially available one from e.g., Sigma-Aldrich can be used. The concentration of pregnenolone to be used in the present invention in the medium is 0.01 μM to 10 μM, preferably 0.05 μM to 5 μM and more preferably 0.1 μM to 2.5 μM.

In the present invention, the adrenergic agonist refers to a substance that can directly bind to an adrenergic receptor and act, preferably a substance binding to at least an α1 acceptor, for example, an agent selected from the group consisting of adrenaline, noradrenaline, etilefrine, naphazoline, phenylephrine, methoxamine and midodrine. A preferable adrenergic agonist in the present invention is an agent selected from the group consisting of etilefrine, phenylephrine and methoxamine. When etilefrine, phenylephrine or methoxamine is used in the present invention, the concentration thereof in the medium is 0.01 μM to 10 μM, preferably 0.05 μM to 5 μM and more preferably 0.1 μM to 2.5 μM.

The upper limit in the number of days for carrying out the step of producing hepatocytes from hepatoblasts in the present invention is not particularly specified since the production efficiency of hepatocytes is not particularly influenced even if culture is carried out for a long period; however, for example, 4 days or more, 5 days or more, 6 days or more, 7 days or more, 8 days or more, 9 days or more, 10 days or more, 11 days or more, 12 days or more, 13 days or more or 14 days or more is mentioned. More preferably, 4 days or more and 12 days or less, in other words, 8 days is mentioned.

In the step of producing hepatocytes from hepatoblasts in the present invention, the culture temperature is not particularly limited and may be about 30 to 40° C. and preferably about 37° C. Culture is carried in a $CO_2$ containing air atmosphere. The $CO_2$ concentration is preferably about 2 to 5%.

The hepatoblasts of the present invention may be produced from endodermal cells. In producing hepatoblasts from endodermal cells, the step of culturing the endodermal cells in a medium containing dimethylsulfoxide (DMSO) can be included.

In the present invention, the endodermal cells refer to cells that are differentiated into cells forming the tissues of organs such as gastrointestinal tract, lung, thyroid, pancreas and liver. Examples may include cells expressing a genetic marker such as SOX17, FOXA2 or CXCR4. SOX17-positive cells are preferable.

In the method of the present invention, the endodermal cells may be provided as a cell population containing endodermal cells and cells other than endodermal cells or a purified cell population, and preferably as a cell population containing 50% or more, 60% or more, 70% or more, 80% or more, 90% or more or 100% of endodermal cells. As a method for purifying endodermal cells, for example, a method including staining the endodermal cells with an antibody against a genetic marker such as SOX17, FOXA2 or CXCR4, and concentrating the stained cells by a flow cytometer (FACS) or a magnetic cell separation device (MACS) is mentioned. More preferably, a method of using an antibody against CXCR4 is mentioned. As the antibody against CXCR4, a commercially available antibody can be appropriately used.

When a cell population containing endodermal cells is provided in a state of being attached to a culture dish, the step of the invention can be carried out by replacing the medium for the cell population containing endodermal cells with a medium containing DMSO. In contrast, when a culture of a cell population containing endodermal cells is provided in a suspension state in a medium, the medium for a culture of the cell population containing endodermal cells is replaced with a medium containing DMSO and the culture may be carried out as it is in the suspension culture conditions. Alternatively, a cell population containing endodermal cells may be subjected to adhesion culture in a medium containing DMSO by using a coated culture dish.

In the present invention, culturing endodermal cells in a suspension condition means that cells are cultured not in contact with a culture dish. Although it is not particularly limited, the culture can be carried out by using a culture dish to which an artificial treatment (for example, treatment such as coating with an extracellular matrix) for improving the adhesion between the cells and the culture dish is not applied or a culture dish artificially treated so as to suppress adhesion (for example, coating treatment with polyhydroxyethyl methacrylate (poly-HEMA)).

In the present invention, the phrase "endodermal cells are adhesion-cultured" means that endodermal cells are cultured by using a coated culture dish. Examples of coating agents may include matrigel (BD Biosciences), Synthemax (Corning), collagen, gelatin, laminin (for example, laminin 111, 411 or 511, or fragments of these), heparan sulfate proteoglycan or entactin and a combination thereof. Preferably, the coating agent is matrigel, Synthemax or gelatin.

In culturing endodermal cells, if the endodermal cells are provided in the form of cell mass in which endodermal cells mutually adhere, the endodermal cells may be substantially separated (dissociated) into single cells by some sort of means and then cultured. Alternatively, culture can be carried out in the state of a cell mass in which the cells mutually adhere. As the separation method, for example, mechanical separation and separation using a separation solution having a protease activity and a collagenase activity (for example, solution containing trypsin and collagenase, i.e., Accutase™ and Accumax™ (Innovative Cell Technologies, Inc.)) or a separation solution having a collagenase activity alone may be mentioned.

The medium to be used in the step of culturing endodermal cells to obtain hepatocytes according to the present invention can be prepared by appropriately adding DMSO to a basic medium for use in culturing animal cells. Examples of the basic medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium and mixture of these mediums. The basic medium may or may not contain serum (for example, fetal bovine serum (FBS)). A serum-free medium may contain, if necessary, one or more serum replacements such as albumin, transferrin, KnockOut Serum Replacement (KSR) (serum substitute for culturing ES cells) (Invitrogen), N2 supplement (Invitrogen), B27 supplement (Invitrogen), a fatty acid, insulin, a collagen precursor, a trace element, 2-mercaptoethanol and 3'-thiol glycerol. The medium may also contain one or more substances such as a lipid, an amino acid, L-glutamine, GlutaMAX (Invitrogen), a nonessential amino acid (NEAA), a vitamin, a growth factor, an antibiotic, an antioxidant, pyruvic acid, a buffer, an inorganic salt, and equivalents to these. In an embodiment, the basic medium is a medium prepared by adding KSR, L-glutamine, NEAA, 2-mercaptoethanol and an antibiotic to DMEM medium.

In the present invention, as DMSO, a commercially available one from e.g., Sigma-Aldrich can be used. The concentration of DMSO to be used in the present invention in the medium is 0.01% to 10%, preferably 0.1% to 5% and more preferably 1%.

The upper limit in the number of days for carrying out the step of producing hepatoblasts from endodermal cells in the present invention is not particularly limited since the production efficiency of hepatocytes is not particularly influenced even if culture is carried out for a longer period and may be, for example, 4 days or more, 5 days or more, 6 days or more, 7 days or more, 8 days or more, 9 days or more, or 10 days or more. More preferably, the step of producing hapetoblasts from endodermal cells may be carried out for 4 days or more and 7 days or less.

In the step of producing hepatoblasts from endodermal cells in the present invention, the culture temperature is not particularly limited and may be about 30 to 40° C. and preferably about 37° C. Culture is carried in a $CO_2$ containing air atmosphere. The $CO_2$ concentration is preferably about 2 to 5%.

In the present invention, endodermal cells may be produced from pluripotent stem cells. Examples of methods for producing endodermal cells from pluripotent stem cells may include a method of activating activin A and the Wnt signal transducing pathway of the cells, a method of activating the Wnt signal transducing pathway of the cells under adhesion culture condition (WO2007/050043) and a method of culturing pluripotent stem cells together with feeder cells (for example, M15 cells) (WO2006/126574). The documents described in this paragraph are herein incorporated by reference.

A more preferable method for producing endodermal cells from pluripotent stem cells is a method including the step of culturing pluripotent stem cells in a medium containing Activin A and a GSK-3β inhibitor. A further preferable method is a method further containing the step of culturing the cells in a medium containing Activin A, a GSK-3β inhibitor and a histone deacetylase (HDAC) inhibitor. More specifically, the method including the following steps:

(1) culturing pluripotent stem cells in a medium containing Activin A and a GSK-3β inhibitor;

(2) culturing the cultured cells obtained in (1) in a medium containing Activin A, a GSK-3β inhibitor and a HDAC inhibitor; and (3) culturing the cultured cells obtained in (2) in a medium containing Activin A and a GSK-3β inhibitor.

The present invention also provides a method for producing hepatocytes from pluripotent stem cells, including the aforementioned steps. More specifically, a method for producing hepatocytes from pluripotent stem cells, including the following steps (i) to (iii):

(i) culturing pluripotent stem cells in a medium containing Activin A and a GSK-3β inhibitor, (ii) culturing the cells obtained in step (i) in a medium containing DMSO, and (iii) culturing the cells obtained in step (ii) in a medium containing an agent selected from the group consisting of pregnenolone and an adrenergic agonist.

In the method of the present invention, in producing endodermal cells from pluripotent stem cells, the pluripotent stem cells may be substantially separated (dissociated) by some sort of means and then cultured. Alternatively, culture can be carried out in the state of a cell mass in which the cells mutually adhere. Preferably, separated cells are cultured. Cell masses may be separated into single cells by means of mechanical separation or by means of a separating solution such as a solution having collagenase and protease activity, for example, a solution containing trypsin and collagenase, i.e., Accutase™ and Accumax™ (Innovative Cell Technologies, Inc.) or a solution having a collagenase activity alone.

Pluripotent stem cells may be cultured by suspension culture or adhesion culture using a coated culture dish, and preferably by adhesion culture.

In the method of the present invention, the suspension culture of pluripotent stem cells refers to culturing the cells not in contact with the culture dish. Although it is not particularly limited, the culture can be carried out by using a culture dish to which an artificial treatment, for example, a treatment such as coating with an extracellular matrix for improving the adhesion between the cells and the culture dish is not applied or a culture dish artificially treated so as to suppress adhesion, for example, coating with polyhydroxyethyl methacrylate (poly-HEMA)).

In the method of the present invention, the adhesion culture refers to culturing cells in a culture dish to which an artificial coating for improving adhesion is provided. Examples of coating agents may include matrigel (BD Biosciences), Synthemax (Corning), collagen, gelatin, laminin, preferably e.g., laminin 111, 411 or 511 or fragments of them, heparan sulfate proteoglycan, or entactin, and a combination thereof. Preferably, the coating agent may be matrigel, Synthemax or gelatin.

The medium to be used in the step of culturing pluripotent stem cells to obtain endodermal cells according to the present invention can be prepared by adding Activin A, a GSK-3β inhibitor or an HDAC inhibitor to a basic medium for culturing animal cells. Examples of the basic media include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium and a mixture of these mediums. These basic mediums may or may not contain serum (for example, fetal bovine serum (FBS)). A serum-free medium may contain, if necessary, one or more serum replacement such as albumin, transferrin, KnockOut Serum Replacement (KSR) (serum substitute for culturing ES cells) (Invitrogen), N2 supplement (Invitrogen), B27 supplement (Invitrogen), a fatty acid, insulin, a collagen precursor, a trace element, 2-mercaptoethanol and 3'-thiol glycerol. The medium also may contain one or more substances such as a lipid, an amino acid, L-glutamine, GlutaMAX (Invitrogen), a nonessential amino acid (NEAA), a vitamin, a growth factor, an antibiotic, an antioxidant, pyruvic acid, a buffer, an inorganic salt, and equivalents to these. In an embodiment, a basic medium is a medium prepared by adding B27 supplement and an antibiotic(s) to RPMI 1640 medium.

In the present invention, examples of Activin A include Activin A derived from human and other animals, a functional variant of these and, for example, a commercially available one from R&D systems. The concentration of Activin A in the medium to be used in this step is 1 ng/ml to 1000 ng/ml, preferably 10 ng/ml to 500 ng/ml, more preferably 50 ng/ml to 200 ng/ml and more preferably 90 ng/ml to 100 ng/ml.

In the present invention, the GSK-3β inhibitor is not particularly limited as long as it can inhibit the function of GSK-3β, for example, kinase activity. Examples thereof include an indirubin derivative, i.e., BIO (also called a GSK-3β inhibitor IX; 6-bromoindirubin 3'-oxime), a maleimide derivative, i.e., SB216763 (3-(2,4-dichlorophenyl)-4-(1-methyl-1H-indol-3-yl)-1H-pyrrole-2,5-dione), phenyl α-bromomethyl ketone compound, i.e., GSK-3β inhibitor VII (4-dibromoacetophenone), a cell-membrane permeable type phosphorylated peptide, i.e., L803-mts (also called a GSK-3β peptide inhibitor; Myr-N-GKEAPPAP-PQSpP-NH$_2$) and CHIR99021 having high selectivity (Nature (2008) 453: 519-523, this document is herein incorporated by reference). These compounds are available, for example, from companies: Stemgent, Calbiochem and Biomol, and may be produced by those skilled in the art. As a GSK-3β inhibitor to be preferably used in this step, CHIR99021 is mentioned. The concentration of the GSK-3β inhibitor to be used in this step can be appropriately selected by those skilled in the art in accordance with the GSK-3β inhibitor to be used. For example, if CHIR99021 is used as the GSK-3β inhibitor, the concentration thereof in a medium is 0.01 μM to 100 μM, preferably 0.1 μM to 10 μM and further preferably 1 μM to 3 μM.

In the present invention, examples of the HDAC inhibitor include valproic acid (VPA), trichostatin, NaB, Vorinostat, NCC-149, NCH-47, NCH-51, MS-275, FK228, Apicidin and MGCD-0103. As these compounds, commercially available ones from company: Sigma-Aldrich can be used. NaB is preferably used. The concentration of NaB to be used in this step is 10 μM to 10 mM, preferably 100 μM to 1 mM and more preferably 0.3 mM to 0.5 mM.

In the present invention, when pluripotent stem cells provided in the form of mass are separated into single cells, the medium containing Activin A and a GSK-3β inhibitor to be used in the step of first culturing the pluripotent stem cells may contain a ROCK inhibitor. The ROCK inhibitor is not particularly limited as long as it can suppress the function of Rho-kinase (ROCK). Examples thereof include Y-27632 (see, for example, Ishizaki et al., Mol. Pharmacol. 57, 976-983 (2000); Narumiya et al., Methods Enzymol. 325, 273-284 (2000)), Fasudil/HA1077 (see, for example, Uenata et al., Nature 389: 990-994 (1997)), H-1152 (see, for example, Sasaki et al., Pharmacol. Ther. 93: 225-232 (2002)), Wf-536 (see, for example, Nakajima et al., Cancer Chemother Pharmacol. 52 (4): 319-324 (2003)) and derivatives of these and an antisense nucleic acid to ROCK, RNA-mediated interference inducible nucleic acid (e.g., siRNA), dominant negative mutants and expression vectors of these. As the ROCK inhibitor, other low molecular compounds known in the art can be used (see, for example, U.S. Application Serial Nos. 2005/0209261, 2005/0192304, 2004/0014755, 2004/0002508, 2004/0002507, 2003/0125344, 2003/0087919 and International Application WO Nos. 2003/062227, 2003/059913, 2003/062225, 2002/076976, 2004/039796). In the present invention, one or two or more ROCK inhibitors can be used. As the ROCK inhibitor, Y-27632 can be preferably used in this step. The concentration of the ROCK inhibitor to be used in this step can be appropriately selected by those skilled in the art in accordance with the ROCK inhibitor to be used. For example, if Y-27632 is used as the ROCK inhibitor, the concentration thereof is 0.1 μM to 100 μM, preferably 1 μM to 50 μM and further preferably 5 μM to 20 μM. The documents described in this paragraph are herein incorporated by reference.

The upper limit of the number of days for carrying out the step of producing endodermal cells from pluripotent stem cells in the present invention is not particularly specified since the production efficiency of hepatocytes is not particularly influenced even if culture is carried out for a long period; however, for example, 4 days or more, 6 days or more, 8 days or more, 10 days or more, 11 days or more, 12 days or more, 13 days or more, 14 days or more, 15 days or more, 16 days or more, 17 days or more, 18 days or more, 19 days or more or 20 days or more is mentioned. Preferably the "step (1) of culturing in a medium containing Activin A and a GSK-3β inhibitor" is carried out for one day, the "step (2) of culturing in a medium containing Activin A, a GSK-3β inhibitor and a HDAC inhibitor" is carried out for one day or more and 3 days or less and the "step (3) of culturing in a medium containing Activin A and a GSK-3β inhibitor" is carried out for 2 days or more and 5 days or less.

In the step of producing endodermal cells from pluripotent stem cells of the present invention, the culture temperature is not particularly limited, and may be about 30 to 40° C. and preferably about 37° C. Culture is carried in a $CO_2$ containing air atmosphere. The $CO_2$ concentration is preferably about 2 to 5%.

In the present invention, the pluripotent stem cells refer to stem cells having not only pluripotency, which is a potential to differentiate into a number of cells existing in living organisms but also a proliferative capacity and include any types of cells as long as they are induced into hepatocytes used in the present invention. Examples of the pluripotent stem cells include, but are not particularly limited to, embryonic stem (ES) cells, embryonic stem (ntES) cells derived from a cloned embryo obtained by nuclear transplantation, spermatogonial stem cells ("GS cells"), embryonic germ cells ("EG cells"), induced pluripotent stem (iPS) cells and multipotent cells derived from cultured fibroblasts or bone marrow stem cells (Muse cells). As the pluripotent stem cells, ES cells and iPS cells such as human iPS cells are particularly used.

Methods for producing iPS cells are known in the art. The iPS cells can be produced by introducing reprogramming factor(s) into somatic cells. As the reprogramming factors herein, genes or gene products such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 or Glis1 are mentioned. These reprogramming factors may be used alone or in combination. Examples of the combination of the reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO 2010/056831, WO2010/068955, WO2010/098419, WO2010/102267, WO 2010/111409, WO 2010/111422, WO2010/115050, WO2010/124290, WO2010/147395, WO2010/147612, Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotechnol., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474: 225-9. The documents described in this paragraph are herein incorporated by reference.

Non-limiting examples of the somatic cells include fetus (calf) somatic cells, somatic cells of newborn baby (calf) and healthy or diseased matured somatic cells and also include all of primary cultured cells, passage cells and established cells. Specific examples of the somatic cells include (1) tissue stem cells (somatic stem cells) such as neural stem cells, hematopoietic stem cells, mesenchymal stem cells and dental pulp stem cells, (2) tissue precursor cells and (3) differentiated cells such as lymphocytes, epithelial cells, endothelial cells, muscle cells, fibroblasts (e.g., dermal cells), hair cells, hepatocytes, gastric mucosa cells, intestinal cells, splenocytes, pancreatic cells (e.g., pancreatic exocrine cells), brain cells, lung cells, kidney cells and adipocytes.

When the hepatocytes obtained are used as a material of cells for transplantation, iPS cells for use in producing the stem cells are desirably produced from somatic cells having the same or substantially the same HLA genotype as that of the individual (recipient) to be implanted, in view of avoiding rejection. The "substantially the same" herein means that the HLA genotype is almost the same to the extent that the immune response to the implanted cells can be suppressed by an immunosuppressant. For example, somatic cells having identical three loci of HLA-A, HLA-B and HLA-DR or four loci of those plus HLA-C with the recipient (in view of HLA type) are preferably used.

The present invention provides a therapeutic agent for a liver disease containing the hepatocytes obtained by a method as mentioned above. The hepatocytes may be a cell population containing hepatocytes and cells other than hepatocytes or a cell population purified for hepatocytes, for example, albumin-positive cells, and preferably a cell population containing 20% or more, 30% or more, 40% or more or 50% or more of hepatocytes. The hepatocytes may be purified by, for example, staining the hepatocytes with an antibody against albumin or a human hepatocyte-specific antibody K8216 (WO2003/080670, this document is herein incorporated by reference) and concentrating the stained cells by a flow cytometer (FACS) or a magnetic cell separation device (MACS).

Examples of methods for administering the therapeutic agent to a patient are as follows: the hepatocytes obtained are formed into a sheet and the sheet is attached to the patient's liver; the hepatocytes obtained are suspended in e.g., saline and the suspension is directly implanted to the patient's liver; and the hepatocytes obtained are three-dimensionally cultured on a scaffold constituted of e.g., matrigel and the resultant hepatocyte mass is implanted.

In the present invention, the number of hepatocytes contained in a therapeutic agent for a liver disease is not particularly limited as long as the implant can be engrafted after the administration and may be appropriately controlled in accordance with the size of the affected area and the size of the body.

Using the hepatocytes prepared by the method of the present invention, metabolism of a test substance can be evaluated in vitro. As the hepatocytes to be used in the test, a hepatocyte population containing hepatocytes and cells other than hepatocytes or a cell population purified for hepatocytes, for example, albumin-positive cells may be used. For example, a cell population containing 20% or more, 30% or more, 40% or more or 50% or more of hepatocytes is used. The purified hepatocytes used in vitro tests can be obtained not only by the aforementioned purification method using an antibody but also by a method of detecting a marker gene by using cells having the marker gene functionally linked to a promoter of an albumin gene. In the present invention, the "marker gene" refers to a protein serving as an index as a result of translation in a cell. Examples thereof include, but are not limited to, a fluorescence protein, a photoprotein, a protein supporting emission of fluorescence, luminescence or color and a protein encoded by a drug-resistant gene.

In the present invention, examples of the fluorescence protein include, but are not limited to, blue fluorescence proteins such as Sirius, BFP and EBFP; cyan fluorescence proteins such as mTurquoise, TagCFP, AmCyan, mTFP1, MidoriishiCyan and CFP; green fluorescence proteins such as TurboGFP, AcGFP, TagGFP, Azami-Green (for example, hmAG1), ZsGreen, EmGFP, EGFP, GFP2, and HyPer; yellow fluorescence protein such as TagYFP, EYFP, Venus, YFP, PhiYFP, PhiYFP-m, TurboYFP, ZsYellow and mBanana; orange fluorescence proteins such as KusabiraOrange (for example, hmKO2) and mOrange; red fluorescence proteins such as TurboRFP, DsRed-Express, DsRed2, TagRFP, DsRed-Monomer, AsRed2 and mStrawberry; and near-infrared fluorescence proteins such as TurboFP602, mRFP1, JRed, KillerRed, mCherry, HcRed, KeimaRed (for example, hdKeimaRed), mRasberry and mPlum.

In the present invention, examples of the photoprotein include, but are not limited to, aequorin. Examples of the protein supporting emission of fluorescence, luminescence or color include, but are not limited to, enzymes decomposing precursors involved in emission of fluorescence, luminescence or color, such as luciferase, phosphatase, peroxidase and β lactamase.

In the present invention, as the protein encoded by a drug-resistant gene, any protein may be used as long as it is resistant to the corresponding drug. In the present invention, examples of the drug-resistant gene include, but are not limited to, antibiotic resistant genes. Examples of the antibiotic resistant genes include a kanamycin resistant gene, an ampicillin resistant gene, a puromycin resistant gene, a blasticidin resistant gene, a gentamicin resistant gene, a kanamycin resistant gene, a tetracycline resistant gene and a chloramphenicol resistant gene.

In the present invention, the cells having a marker gene functionally linked to the promoter of an albumin gene can be prepared by introducing a vector in which the marker gene is functionally linked to a side downstream of the promoter region of the albumin gene, into the cell in accordance with a customary method. The vector may be simply introduced in the cells or the marker gene may be integrated into the albumin locus by homologous recombination.

The test for evaluating the metabolism of a test substance includes the steps of: (i) bringing a test substance into contact with the hepatocytes obtained by the method of the present invention and (ii) detecting the metabolite of the test substance. The "contact" in the step (i) is carried out by adding a test substance to a medium for use in culturing the hepatocytes produced by the method of the present invention. The timing of adding a test compound is not particularly limited. Accordingly, after culture is initiated in a test substance-free medium, the test substance may be added at any time-point or culture may be initiated in a medium already containing a test substance.

Examples of the test substance include components already used in e.g., pharmaceuticals and nutritious food or candidate components. At least two types of test substances may be simultaneously added to check interaction and synergistic action of the test substances. The test substances may be derived from natural products or synthesized. In the latter case, if e.g., a combinatorial synthesis method is used, an efficient assay system can be constructed.

The period of allowing contact of a test substance can be arbitrarily set. The contact period is, for example, 10 minutes to 3 days and preferably one hour to one day. Contact is divided into a plurality of times.

The metabolism of a test substance refers to chemical modification of a test substance through e.g., hydrolysis of e.g., an ester, an oxidation reaction (particularly, oxidation by cytochrome P450) and a reduction reaction. Whether metabolism is made or not can be found by detecting, for example, a metabolite. Preferably, after the step (i), the culture medium obtained is used as a sample and a prospective metabolite is qualitatively or quantitatively measured. The measuring method may be appropriately selected in accordance with a test substance and its prospective metabolite; for example, mass spectrometry, liquid chromatography, immunological method (for example, fluorescence immunoassay (FIA), enzyme immunoassay (EIA)) can be employed.

Typically, when the metabolite of a test substance is detected, it is determined that "a test substance was metabolized". In addition, the amount of metabolized test substance can be evaluated by the amount of the metabolite.

In addition, induction of expression of a drug metabolizing enzyme (for example, cytochrome, UGT) can be confirmed by the hepatocytes obtained by the present invention. The expression of a drug metabolizing enzyme can be evaluated by confirming the mRNA or protein. For example, when an increase of mRNA of a drug metabolizing enzyme is found, it can be determined that "the test substance is suspected to cause drug interaction".

The toxicity of a test substance can be confirmed by using the hepatocytes prepared by the method of the present invention. This embodiment comprise the steps of: (i) bringing a test substance into contact with the hepatocytes obtained by the method of the present invention and (ii) examining the state of hepatocytes after the step (i) is carried out. The step (i) is the same as in the above mentioned test for evaluating the metabolism of a test substance.

In the step (ii), the state of the hepatocytes which were in contact with the test substance is observed and the toxicity of the test substance is evaluated. The state of the hepatocytes can be found by e.g., survival rate, morphology and liver toxicity markers (e.g., GOT, GPT) detected in the culture medium. For example, if the survival rate of the cells decreases by the contact with a test substance, it can be determined that "the test substance has hepatotoxicity". Not only when morphological abnormality of the cells is observed by the contact of the test substance but also when the amount of a liver toxicity marker in the culture medium increases, it can be determined that "the test substance has hepatotoxicity". Quantitative determination may be carried out in accordance with the degree of a decrease in the survival rate and the amount of the liver toxicity marker.

The present invention will be more specifically described by way of Examples below. The scope of the present invention is not limited by these Examples.

Example 1

ALBUMINGFP Human iPS Cell Lines

Human iPS cells (201B6, 648A1, 648B1, 604A1, 604B1, 604A3, 606A1, 606B1 and 610B1) were gifted from Prof. Yamanaka of Kyoto University and cultured by a conventional method (Takahashi K, et al. Cell. 131: 861-72). Human iPS cells 201B6 were prepared by the method described in Cell. 131: 861-872, 2007; and human iPS cells 648A1, 648B1, 604A1, 604B1, 604A3, 606A1, 606B1 and 610B1 were prepared by the method described in Okita K, et al., Stem Cells. 31: 458-466, 2013., those documents described in this paragraph are herein incorporated by reference.

Induction of Albumin-Positive Cells
<Stage 1>

Human iPS cells 201B6 were separated into single cells by adding Accutase (Innovative Cell Technologies, AT-104) and seeded in a 24-well plate coated with Matrigel basement Membrane Matrix Growth Factor Reduced (BD) so as to obtain a ratio of $2 \times 10^5$ cells/well, and cultured in RPMI1640 supplemented with 1 μM CHIR99021 (Stemgent), 100 ng/ml Activin A (R&D systems), 2% B27 (Invitrogen) and 0.5% PenStrep (Invitrogen) for one day (Stage 1-1) (day 1).

Subsequently, 0.5 mM NaB (Sigma) was added and culture was made for 3 days (Stage 1-2) (day 4). Then, the medium was removed and culture was made in RPMI1640 containing 1 μM CHIR99021 (Axon Medchem), 100 ng/ml Activin A (R&D systems), 2% B27 (Invitrogen) and 0.5% PenStrep (Invitrogen) for 5 days (Stage 1-3) (day 9). The cells obtained by the above steps were stained with a SOX17 antibody and the content ratio of SOX17 positive cells were determined. A cell population containing 70% to 80% of SOX17 positive cells (endodermal cells) was obtained.

<Stage 2>

After Stage 1, the medium was exchanged with Knockout™ DMEM (Invitrogen) medium supplemented with 1% DMSO, 20% KSR (Invitrogen), 1 mM L-glutamic acid, 1% NEAA (Invitrogen), 0.1 mM β mercaptoethanol and 0.5% PenStrep. Culture was made for 7 days and the resultant cells were stained with an AFP antibody. The content ratio of AFP positive cells was determined. A cell population containing 40% to 60% of AFP positive cells (hepatoblasts) was obtained (day 16).

<Stage 3>

After Stage 2, the medium was exchanged with Hepatocyte Culture Medium (HCM SingleQuots Kit) (LONZA) supplemented with 150 nM or 1 μM pregnenolone (Tokyo Kasei) or methoxamine hydrochloride (Sigma). The cells were cultured for 4 days, 8 days or 12 days. At this time, as a control, cells were cultured in a Hepatocyte Culture Medium (HCM SingleQuots Kit) supplemented with 1% DMSO, or 20 ng/ml HGF and 20 ng/ml oncostatin M (HGF+OsM).

Evaluation of Induced Albumin Positive Cells

Figure 2:
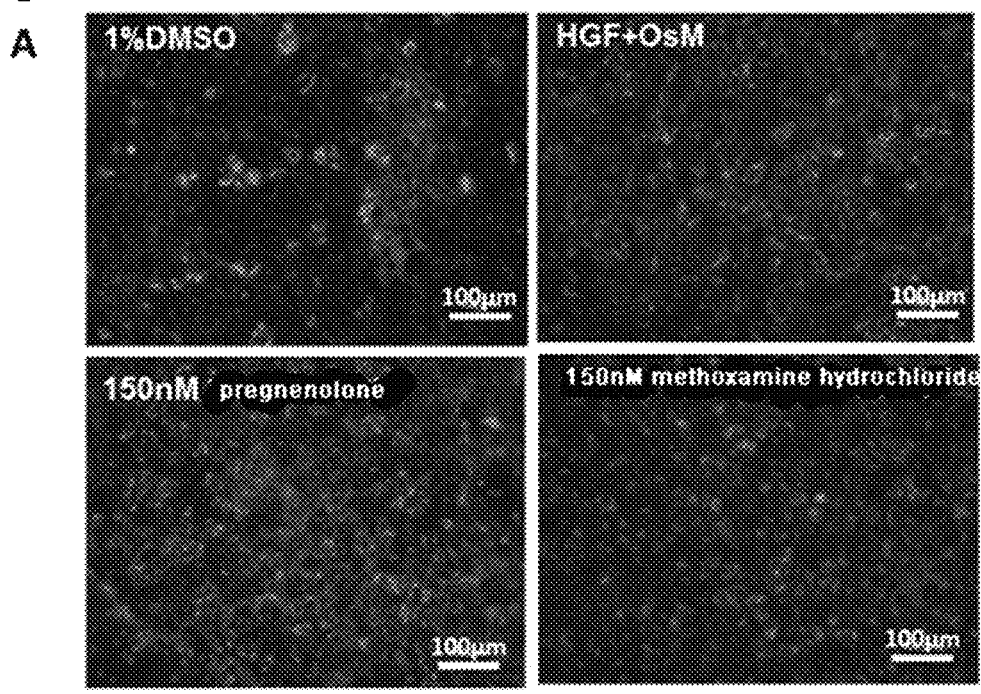
FIG. 2A shows images of cells, which were induced by using individual agents (DMSO, HGF+oncostatin M, methoxamine hydrochloride and pregnenolone) in Stage 3 and immuno-stained with an anti-albumin antibody.
FIG. 2B shows the results of albumin-positive cell content ratios determined in the cases where induction was carried out by using agents (DMSO, HGF+oncostatin M, methoxamine hydrochloride and pregnenolone) in Stage 3.
Figure 2:
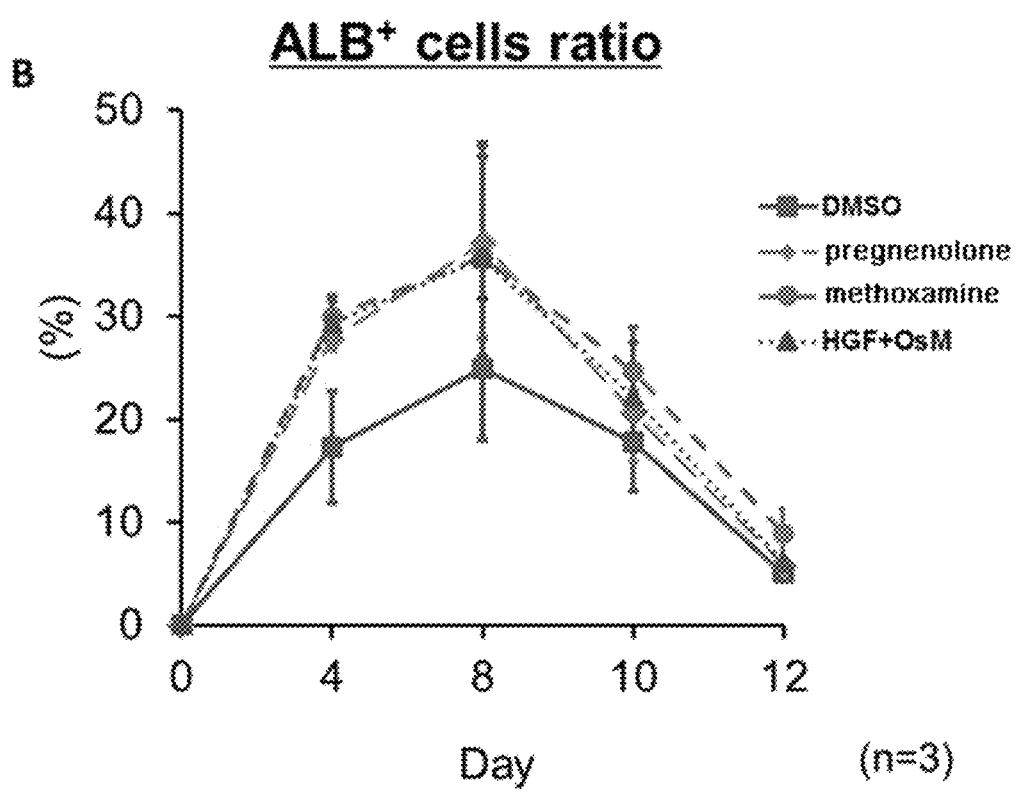
Figure 3:
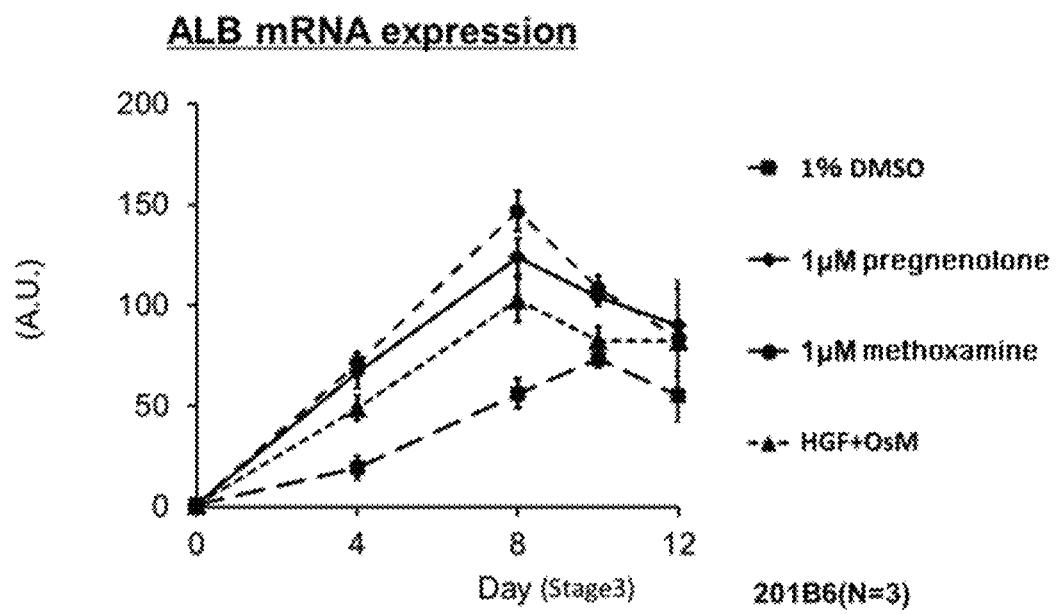
FIG. 3 shows the albumin mRNA expression level measured by q-PCR in the cells induced by using agents (DMSO, HGF+oncostatin M, methoxamine hydrochloride and pregnenolone) in Stage 3. The vertical axis shows a relative fluorescence intensity value, which were determined by correcting the fluorescence intensity values based on the β-actin mRNA expression level as the internal standard and calculating with the corrected intensity value on Day 0 being 1.

The cell groups obtained in Stage 3 were immuno-stained with an anti-albumin antibody (BETHYL, A80-229A) (FIG. 2). The mRNA expression level of albumin was measured by quantitative PCR (FIG. 3). The primers used herein are Foward: 5'-CGCTATTAGTTCGTTACACCA-3' (SEQ ID No: 1) and Reverse: 5'-TTTACAACATTTGCTGCCCA-3' (SEQ ID No: 2). It was found that cells most efficiently expressing albumin were obtained in the case where culture in Stage 3 was carried out for 8 days. The production efficiency of the albumin-producing cells was analyzed based on the ratio of albumin positive cells relative to the number of nuclear staining (DAPI) positive cells, i.e., the ratio of albumin-positive cells, by In cell analyzer (FIG. 2B).

In Stage 3, the same results were obtained at concentrations of pregnenolone of 150 nM and 1 μM.

Example 2

Study on the Days of Culture in Stage 1 and Stage 2

It was found that the similar effects as Example 1 were obtained as to the final yield of albumin-positive cells obtained even if the period of Stage 1-2, i.e. the period for culturing the cells in the presence of NaB in Stage 1, was set to be one day. It was also found that the similar effects as Example 1 were obtained even if the period of Stage 1-3, i.e. the period for culturing the cells in the NaB-free medium in Stage 1 was set to be two days. Hence, it was found that hepatocytes can be induced by carrying out Stage 1 for the period ranging from 4 days to 9 days.

It was further found that if the period for culturing the cells in Stage 2 was set to be 4 days, the same effect as in the case of culture for 7 day was obtained based on the final yield of albumin-positive cells.

Example 3

Search for Alternative Compounds

The effects of analogous compounds (adrenergic receptor agonist, in particular, an agent having α receptor stimulating action) serving as an alternative compound for a methoxamine hydrochloride were checked. In Stage 3 as mentioned above, cells were cultured in a Hepatocyte Culture Medium (HCM SingleQuots Kit) supplemented with 1 μM etilefrine, phenylephrine or methoxamine hydrochloride for 8 days.

Figure 4:
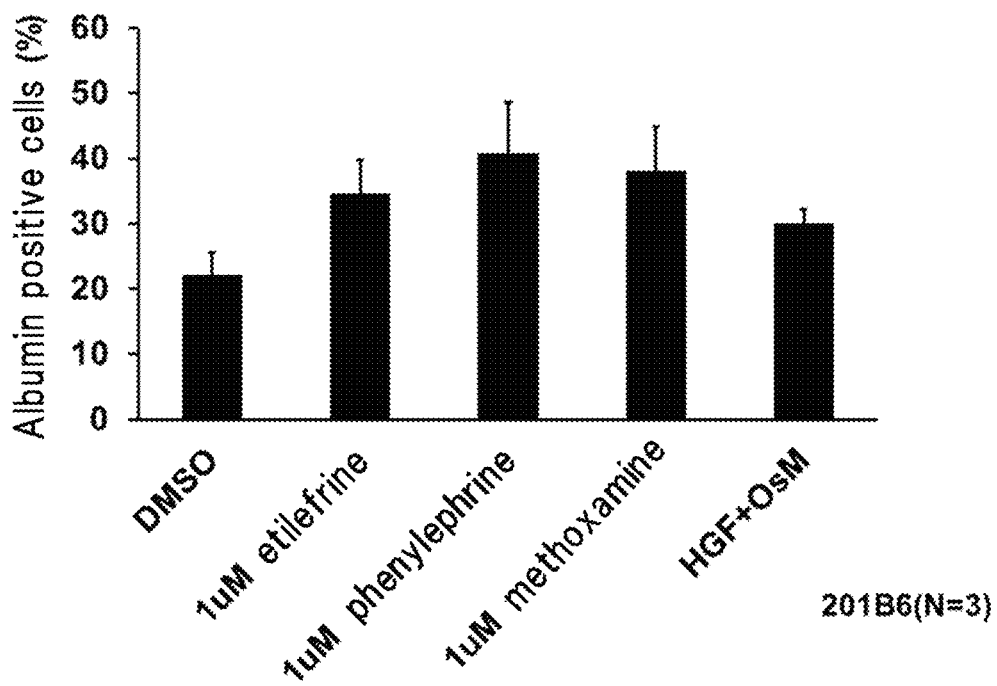
FIG. 4 shows the results of albumin-positive cell content ratios determined in the cells induced by using agents (DMSO, etilefrine, phenylephrine, methoxamine, HGF+oncostatin M) in Stage 3
Figure 5:
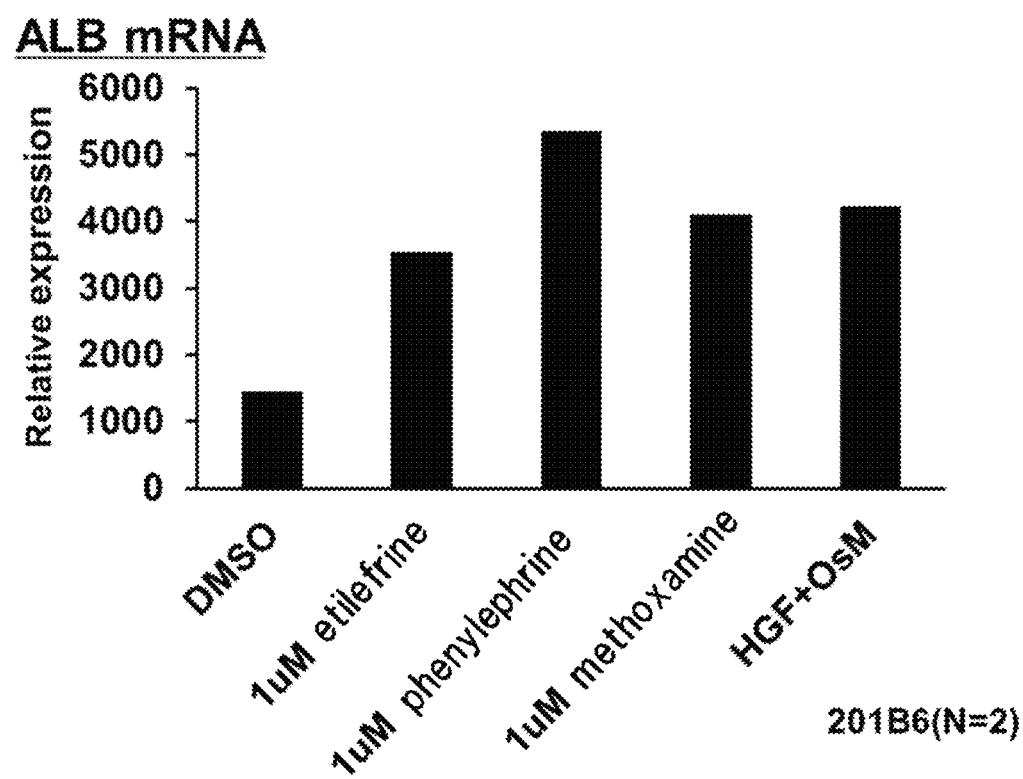
FIG. 5 shows the q-PCR measurement results of the albumin mRNA expression level in the cells induced by using agents (DMSO, etilefrine, phenylephrine, methoxamine, HGF+oncostatin M) in Stage 3. The results are shown as relative values calculated with the value on Day 6 of Stage 2 being 1.
Figure 6:
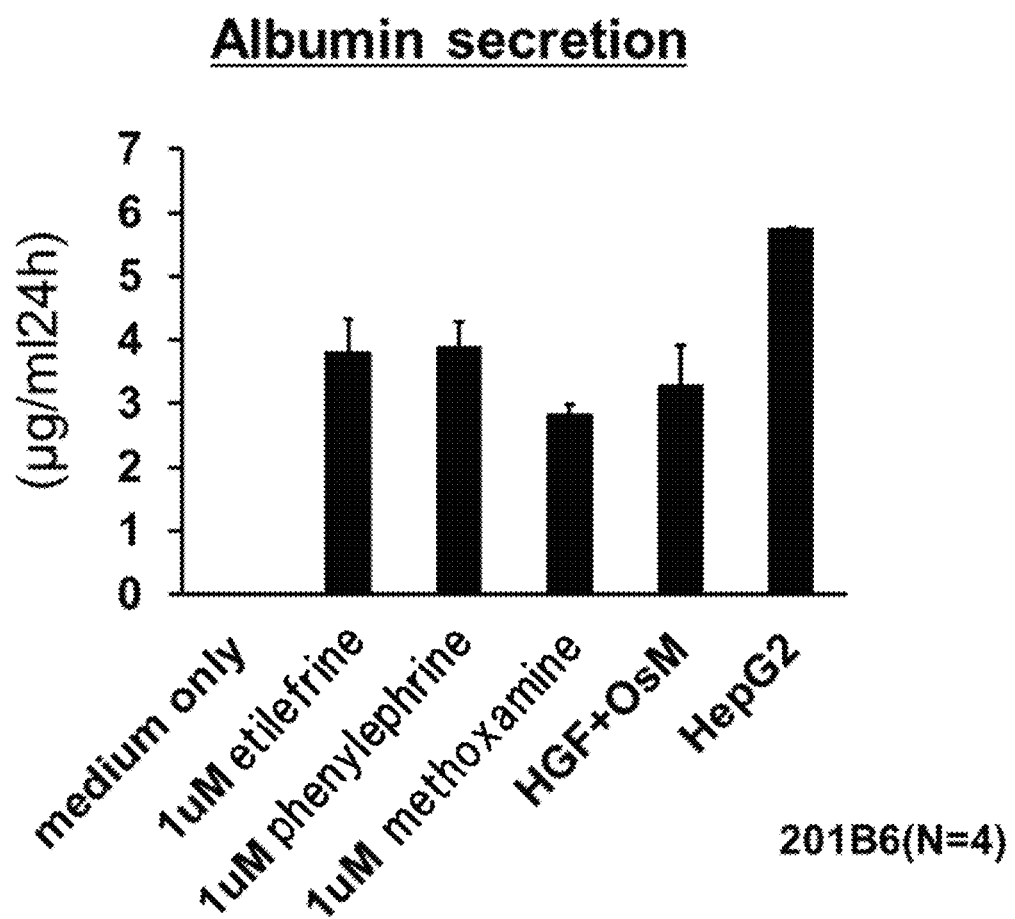
FIG. 6 shows the secretion volume of albumin in cells induced by using agents (medium only (DMSO), etilefrine, phenylephrine, methoxamine, HGF+oncostatin M) in Stage 3. In the figure, HepG2 shows the volume of albumin secretion from a human hepatocarcinoma-derived cell line.

The content ratio of albumin-positive cells and the mRNA expression level of albumin were measured in the same manner as above. It was found that etilefrine and phenylephrine both have the similar effect as methoxamine hydrochloride (FIGS. 4 and 5). Furthermore, the amount of albumin secreted from the obtained cell population into the culture mediumliquid was measured by ELISA. It was found that cells having an ability to secrete albumin can be induced by adding any one of etilefrine, phenylephrine and methoxamine hydrochloride to a medium in Stage 3 (FIG. 6).

From the above results, it was suggested that hepatocytes can be efficiently produced by using a low molecular compound such as pregnenolone or adrenergic receptor agonist in the step of producing hepatocytes from hepatoblasts.

Example 4

Evaluation of Induced Hepatocytes (Drug Metabolizing Enzyme Induction Reaction)

Figure 7:
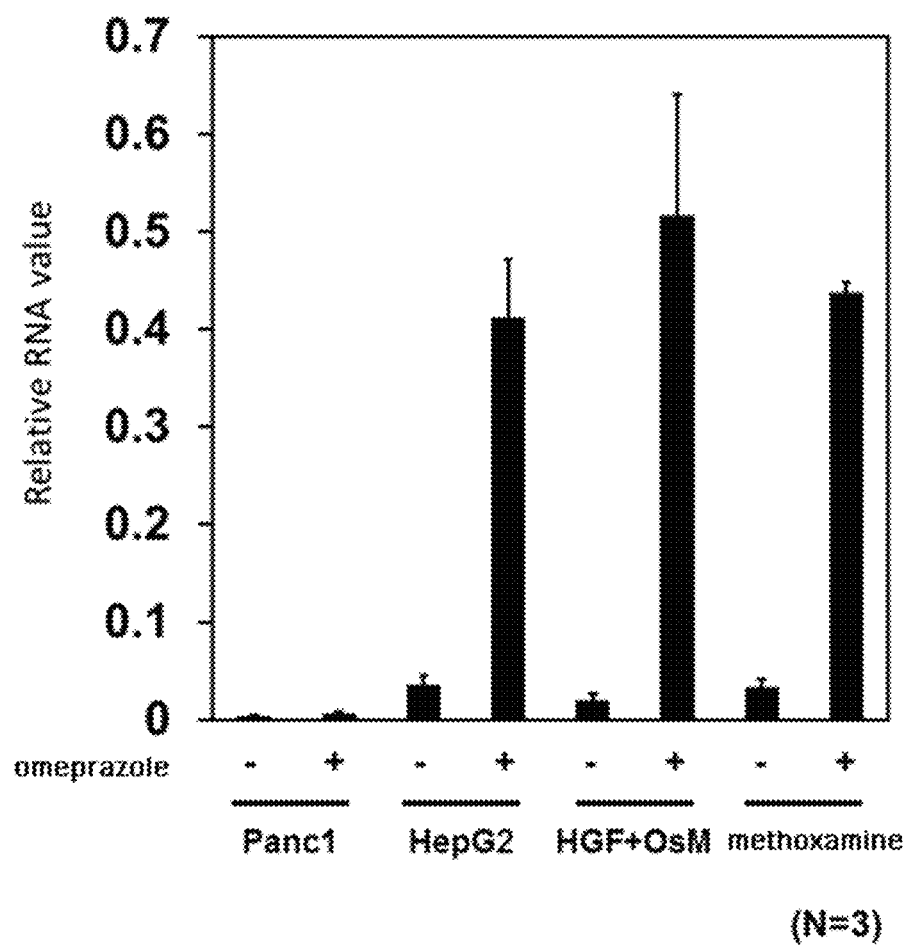
FIG. 7 shows the q-PCR measurement results of CYP1A1 mRNA expression level in Panc1 (human pancreatic cancer-derived cell line), HepG2 (human hepatocarcinoma-derived cell line), cells (HGF+OsM) induced by using HGF+oncostatin M in Stage 3 or a cell induced with 1 μM methoxamine in Stage 3 in the presence (+) or absence (−) of 100 μM omeprazole. The mRNA expression level of CYP1A1 is expressed as a relative value to the expression amount of β actin mRNA.

The period of Stage 1 of the aforementioned method was set to be 6 days (Stage 1-1: 1 day, Stage 1-2: 2 days and Stage 1-3: 3 days) and the period of Stage 2 was set to be 6 days. A cell population obtained by culturing the cell population obtained in Stage 2 in a Hepatocyte Culture Medium (HCM SingleQuots Kit) supplemented with 20 ng/ml HGF and 20 ng/ml oncostatin M (HGF+OsM) for 8 days; and a cell population obtained by culturing the cell population obtained in Stage 2 in a Hepatocyte Culture Medium (HCM SingleQuots Kit) supplemented with 1 μM methoxamine hydrochloride for 8 days; Panc1 (human pancreatic cancer-derived cell line: Riken Bioresource Center); and HepG2 (human hepatocarcinoma-derived cell line) were used. Each of the cell populations was cultured in a Hepatocyte Culture Medium (HCM SingleQuots Kit) in the presence or absence of 100 μM omeprazole (Sigma) for 2 days, and thereafter, CYP1A1 mRNA expression level was measured by quantitative PCR. The primers used herein were Forward: 5'-CCACCAAGAACTGCTTAGCC-3' (SEQ ID No: 3) and Reverse: 5'-CAGCTCCAAAGAGGTCCAAG-3' (SEQ ID No: 4). The amount of CYP1A1 mRNA relative to β actin mRNA was obtained and used as relative expression level of CYP1A1. The relative expression levels of the individual cells are shown in FIG. 7. It was confirmed that expression of CYP1A1 was induced by addition of omeprazole in the cell populations induced from HepG2 cell and the cell population obtained in Stage 2 in the presence of HGF+OsM or methoxamine hydrochloride. In the hepatocytes induced from pluripotent stem cells in the presence of methoxamine, expression of CYP1A1 was induced by omeprazole. From the results, it was suggested that the hepatocytes can be used for evaluating drug interactions.

Evaluation of Induced Hepatocytes (Liver Function Evaluation)

Figure 8:
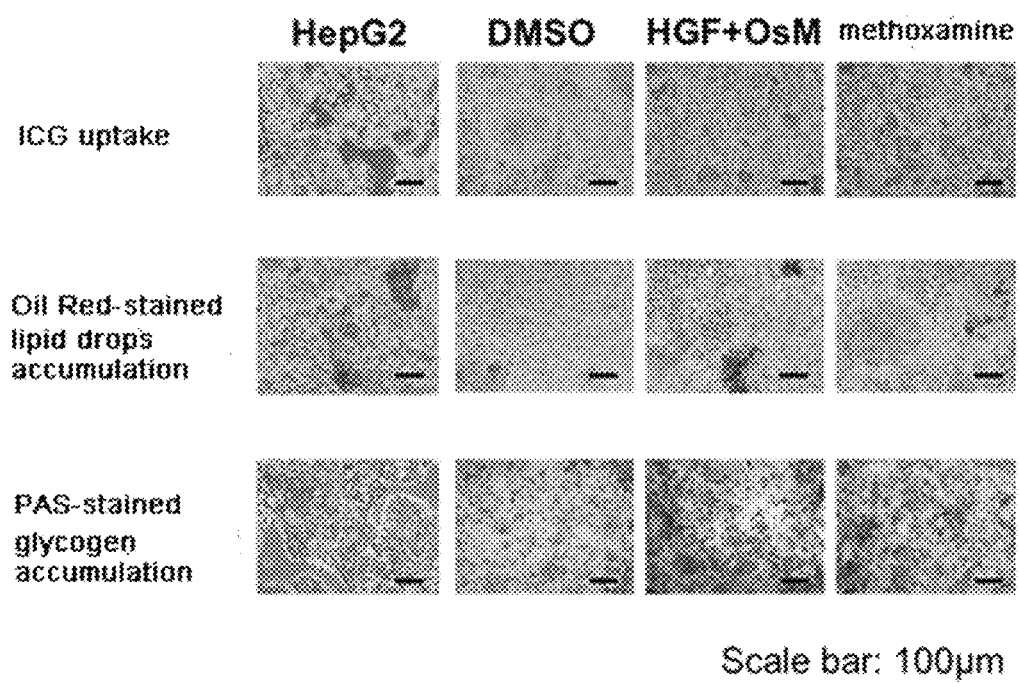
FIG. 8 shows microscope images (upper) of HepG2, cells (DMSO) induced by using DMSO in Stage 3, cells (HGF+OsM) induced by using HGF+oncostatin M in Stage 3 or cells induced by using 1 μM methoxamine in Stage 3, which were cultured for one hour in the presence of 1 mg/ml ICG (Indocyanine green); Oil Red-stained images (middle) of individual cells (HepG2, DMSO, HGF+oncostatin M and methoxamine); and PAS-stained image thereof (lower).

The period of Stage 1 of the aforementioned method was set to be 6 days (Stage 1-1: 1 day, Stage 1-2: 2 days and Stage 1-3: 3 days) and the period of Stage 2 was set to be 6 days. Hepatocytes obtained by carrying out Stage 3 by culturing the cells obtained in Stage 2 in a Hepatocyte Culture Medium (HCM SingleQuots Kit) supplemented with 20 ng/ml HGF and 20 ng/ml oncostatin M (HGF+OsM) for 8 days; a cell population obtained by carrying out Stage 3 by culturing the cells obtained in Stage 2 in a Hepatocyte Culture Medium (HCM SingleQuots Kit) supplemented with 1 μM methoxamine hydrochloride for 8; a cell population obtained by carrying out Stage 3 by culturing the cells obtained in Stage 2 in a Hepatocyte Culture Medium (HCM SingleQuots Kit) supplemented with DMSO for 8 days; and HepG2 cells were used. 1 mg/ml ICG (indocyanine green) (Sigma) was added to each cell population and cultured for 1 hour. Then, ICG uptake by the cells was observed. ICG uptake was observed in HepG2 cells and the cell population induced in the presence of HGF+OsM or methoxamine hydrochloride (FIG. 8, upper). Hence, it was suggested that the cells have a drug metabolizing function.

The cells induced in the presence of HGF+OsM, methoxamine hydrochloride or DMSO and HepG2 were stained with Oil Red. In the cases of HepG2, HGF+OsM, and methoxamine, accumulation of lipid drops was observed in some of the cells (FIG. 8, middle).

The cells induced in the presence of HGF+OsM, methoxamine hydrochloride or DMSO, and HepG2 were stained with PAS. A number of cells in the cell populations induced in the presence of HGF+OsM and methoxamine, as well as in HepG2 cells were stained red-purple (FIG. 8, lower). Hence, it was found that the cells induced in the presence of methoxamine hydrochloride has an ability to accumulate glycogen.

Evaluation of Induced Hepatocytes (Evaluation on Expression of Drug Metabolizing Enzymes)

Figure 9:
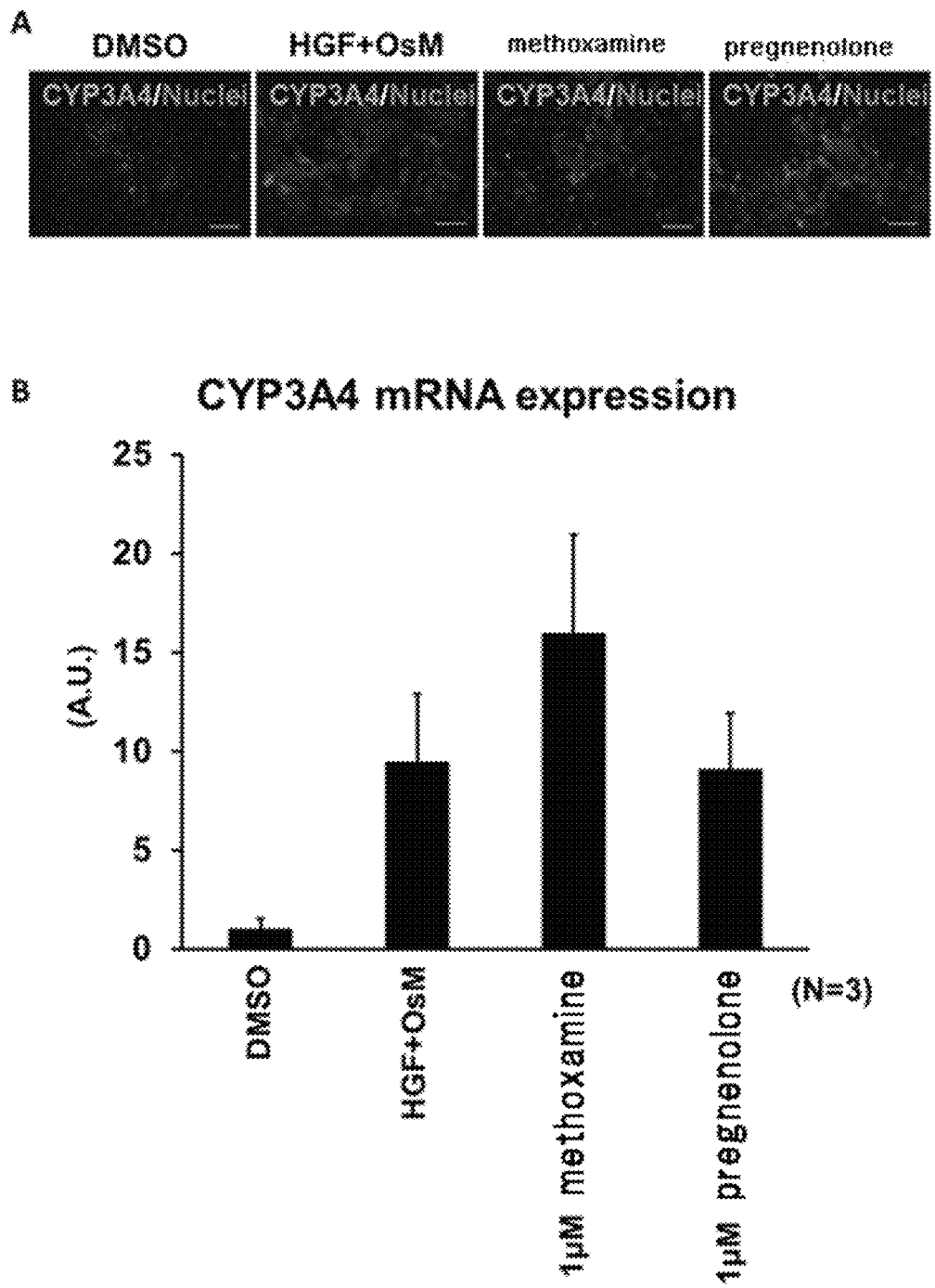
FIG. 9A shows immunostained images of cells induced by using agents (DMSO, HGF+oncostatin M, methoxamine and pregnenolone) in Stage 3 and stained with anti-CYP3A4 antibody.
FIG. 9B shows the q-PCR measurement results of the CYP3A4 mRNA expression levels of cells induced by using agents (DMSO, HGF+oncostatin M, methoxamine and pregnenolone) in Stage 3. The CYP3A4 mRNA expression levels are shown as relative values to the expression level thereof in the cells induced with DMSO.

The period of Stage 1 of the aforementioned method was set to be 6 days (Stage 1-1: 1 day, Stage 1-2: 2 days and Stage 1-3: 3 days) and the period of Stage 2 was set to be 6 days. A cell population obtained by culturing the cells obtained in Stage 2 in a Hepatocyte Culture Medium (HCM SingleQuots Kit) containing 20 ng/ml HGF and 20 ng/ml oncostatin M (HGF+OsM) for 8 days; a cell population obtained by culturing the cells obtained in Stage 2 in a Hepatocyte Culture Medium (HCM SingleQuots Kit) supplemented with 1 µM methoxamine hydrochloride for 8 days; a cell population obtained by culturing the cells obtained in Stage 2 in a Hepatocyte Culture Medium (HCM SingleQuots Kit) supplemented with 1 µM pregnenolone for 8 days; and a cell population obtained by culturing the cells obtained in Stage 2 in a Hepatocyte Culture Medium (HCM SingleQuots Kit) supplemented with DMSO for 8 days were immuno-stained with a CYP3A4 antibody (Proteintech Group) (FIG. 9A). Cells expressing CYP3A4 were found in all cell populations except for that induced with DMSO. CYP3A4mRNA expression levels were measured in these cell populations by quantitative PCR in the same manner as above. In the hepatocytes induced by the substances except DMSO, CYP3A4 was intensively expressed (FIG. 9B). The primers used herein were Forward: 5'-AAGACCCCTTT-GTGGAAAAC-3' (SEQ ID No: 5) and Reverse: 5'-CGAG-GCGACTTTCTTTCATC-3' (SEQ ID No: 6).

From the above results, it was suggested that hepatic metabolism of a test substance can be determined by using the hepatocytes produced by the method of the present invention.

Example 5

Study on the Concentration of Methoxamine

Figure 10:
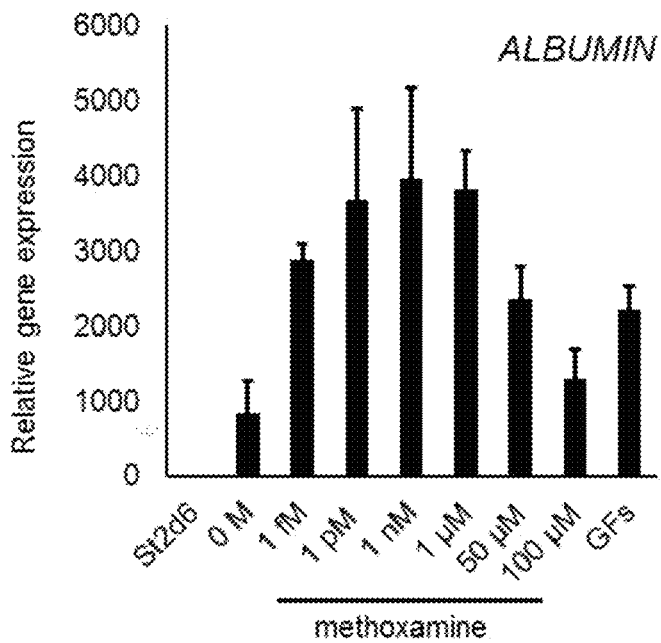
FIG. 10 shows q-PCR measurement results of albumin mRNA expression level in the cases of using methoxamine in different concentrations in Stage 3. In the figure, St2d6 shows the results of Stage 2, Day 6 and GFs shows the results of the case using HGF+oncostatin M.

The period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 8 days. The concentrations of methoxamine hydrochloride added in Stage 3 was set to 0 M, 1 fM, 1 pM, 1 nM, 1 µM, 50 µM or 100 µM. Expression of albumin mRNA in thus obtained cell populations were measured by quantitative PCR (FIG. 10). It was found that albumin-expressing cells were obtained when the concentration of methoxamine hydrochloride was 1 fM or more.

Evaluation of Induced Hepatocytes (Evaluation on Expression of Drug Metabolizing Enzymes)

Figure 11:
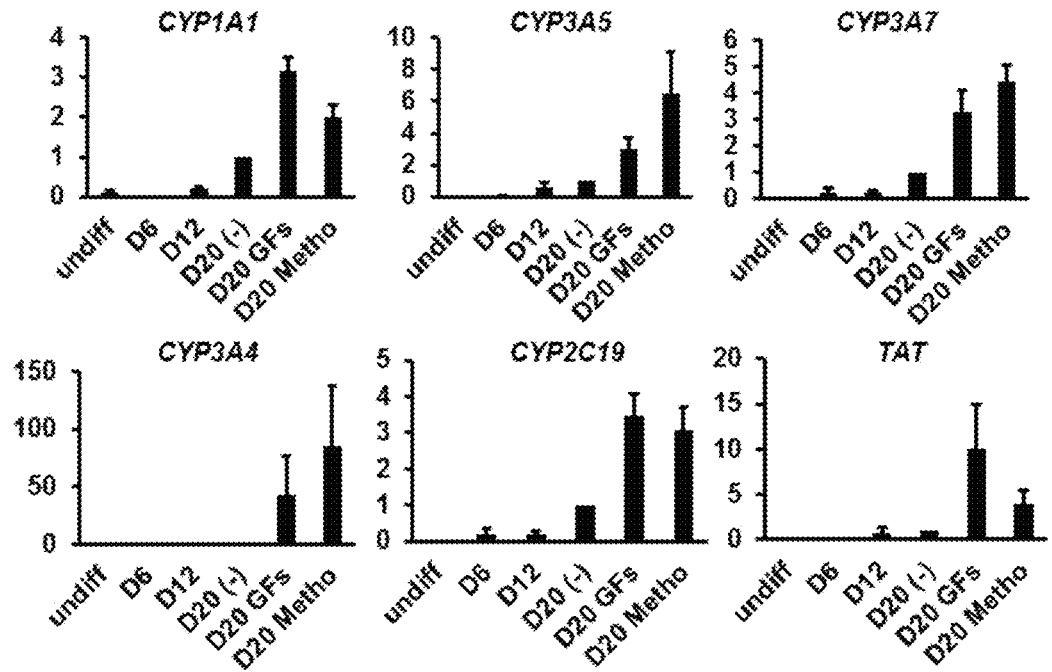
FIG. 11 shows the q-PCR measurement results of CYP1A1, CYP3A5, CYP3A7, CYP3A4, CYP2A19 and TAT mRNA expression levels in the cells induced in different conditions. In the figure, "undiff" shows the results of the iPS cells; D6 shows the results of the cells on Day 6 after differentiation induction; D12 shows the results of the cells on Day 12 after differentiation induction, D20 (−) shows the results of the cells cultured in a Hepatocyte Culture Medium in the absence of additive agents in Stage 3 on Day 20 after differentiation induction; D20 GFs shows the results of the cells cultured in the presence of HGF+oncostatin M in Stage 3 on Day 20 after differentiation induction; and D20 Metho shows the results of the cells cultured in the presence of methoxamine in Stage 3 on Day 20 after differentiation induction.

The period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 8 days. The methoxamine hydrochloride concentration in Stage 3 was set to 1 µM. The expression of drug metabolizing enzymes (CYP1A1, CYP3A5, CYP3A7, CYP3A4, CYP2C19) and tyrosine aminotransferase (TAT) in thus obtained cells were measured by quantitative PCR (FIG. 11). The sequences of the primers used herein are shown in Table 1. It was found that the cell populations prepared by the method of the present invention express drug metabolizing enzymes at the similar level as in the case where HGF+OsM was used in Stage 3.

TABLE 1

| | | |
|---|---|---|
| CYP3A5-Foward | CTCTCTGTTTCCAAAAGATACC | SEQ ID No: 7 |
| CYP3A5-Reverse | TGAAGATTATTGACTGGGCTG | SEQ ID No: 8 |
| CYP3A7-Forward | AGATTTAATCCATTAGATCCATTCG | SEQ ID No: 9 |
| CYP3A7-Reverse | AGGCGACCTTCTTTTATCTG | SEQ ID No: 10 |
| CYP2C19-Forward | GAACACCAAGAATCGATGGACA | SEQ ID No: 11 |
| CYP2C19-Reverse | TCAGCAGGAGAAGGAGAGCATA | SEQ ID No: 12 |
| TAT-Forward | ATCTCTGTTATGGGCGTTG | SEQ ID No: 13 |
| TAT-Reverse | TGATGACCACTCGGATGAAA | SEQ ID No: 14 |

Evaluation on Influence of Drug Interaction

Figure 12:
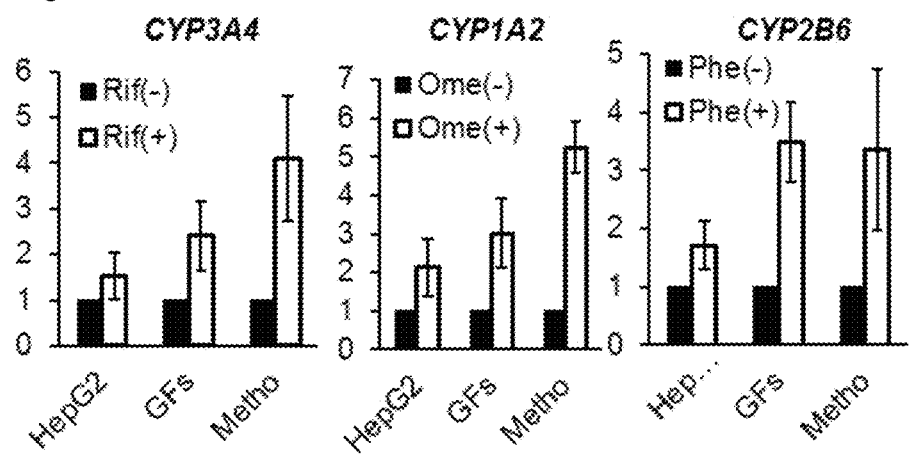
FIG. 12 shows the q-PCR measurement results of CYP3A4, CYP1A2 and CYP2B6 mRNA expression levels of the cells induced in different conditions. CYP3A4 shows the results of the cases where 40 μM rifampicin was added (Rif (+)) or not added (Rif (−)); CYP1A2 shows the results of the cases where 40 μM omeprazole was added (Ome (+)) or not added (Ome (−)); and CYP2B6 shows the results of the cases where 100 μM phenobarbital was added (Phe (+)) or not added (Phe (−)). In the figure, HepG2 shows the results of HepG2 cell; GFs shows the results of differentiated cells induced by adding HGF+oncostatin M in Stage 3; and Metho shows the results of differentiated cells induced by adding methoxamine in Stage 3.

The period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 6 days. The cells were produced accordingly and the effects of drugs on the drug metabolizing enzymes were evaluated with the produced cells. Specifically, 40 µM rifampicin was added to the cells on Day 6 of Stage 3. Two days later, the expression of CYP3A4 mRNA in the cells was measured by quantitative PCR. Similarly, 40 µM omeprazole was added and the expression of CYP1A2 mRNA was measured, and also 100 µM phenobarbital was added and CYP2B6 mRNA was measured. It was found that expression of a drug metabolizing enzyme was induced by contacting the cells prepared by the method of the present invention with the corresponding drug (FIG. 12). Hence, it was suggested that drug interaction can be evaluated with the cells obtained by this invention.

Differentiation of Hepatocytes from iPS Cell Lines

Figure 13:
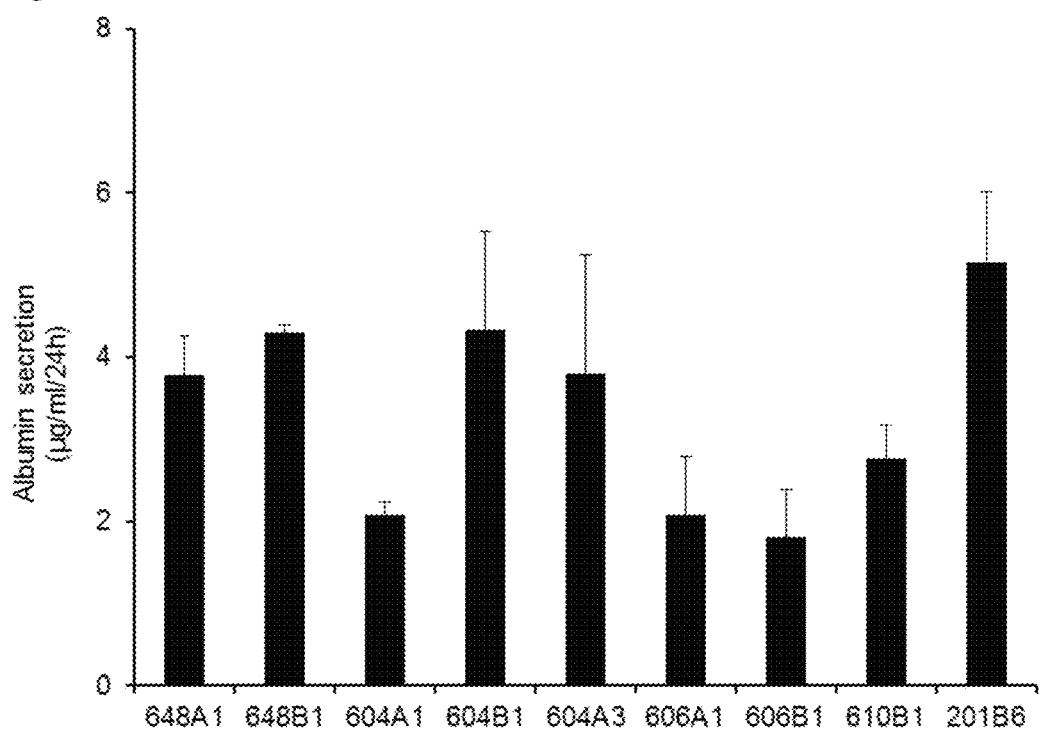
FIG. 13 shows the albumin secretion volumes in the cells induced by the method of the present invention using various iPS cell lines.

The period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 8 days. In the conditions, hepatocytes were induced from iPS cells 648A1, 648B1, 604A1, 604B1, 604A3, 606A1, 606B1 and 610B1. The amounts of albumin secreted from thus induced cells were measured. It was found that cells that secret at least 2 µg/ml of albumin per day were produced from all iPS cell lines examined (FIG. 13).

Determination of Content Ratio of Albumin-Positive Cells

Figure 14:
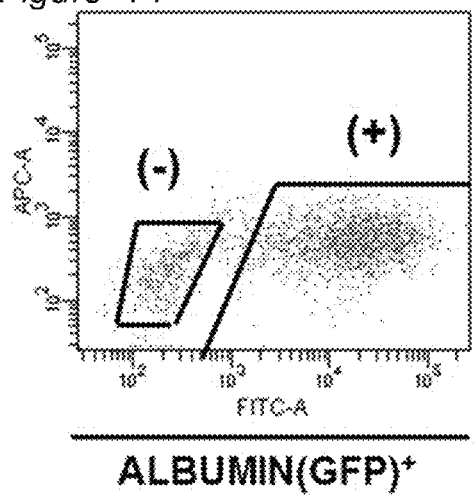
FIG. 14 shows FACS results of cells induced by using iPS cells having GFP integrated downstream of the promoter of albumin (gene) in accordance with the method of the present invention. In the figure, (+) represents a GFP-positive cell group; whereas, (−) represents a GFP negative cell group. The content ratio of the GFP positive cells is 39.9%.

Homologous recombination was carried out according to a conventional method such that GFP-polyA is linked to a site downstream of the start codon of an albumin locus of human iPS cells (201B6) to give a cell line expressing GFP in connection with expression of albumin (hereinafter referred to as albumin reporter iPS cells). Hepatocytes were induced from the albumin reporter iPS cells in the conditions: the period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 8 days and then, the content ratio of the GFP positive cells was determined (FIG. 14). The content ratio of albumin-expressing cells in the induced cell population was 39.9%.

Study on the Mechanism of Hepatocytes Induction

Figure 15:
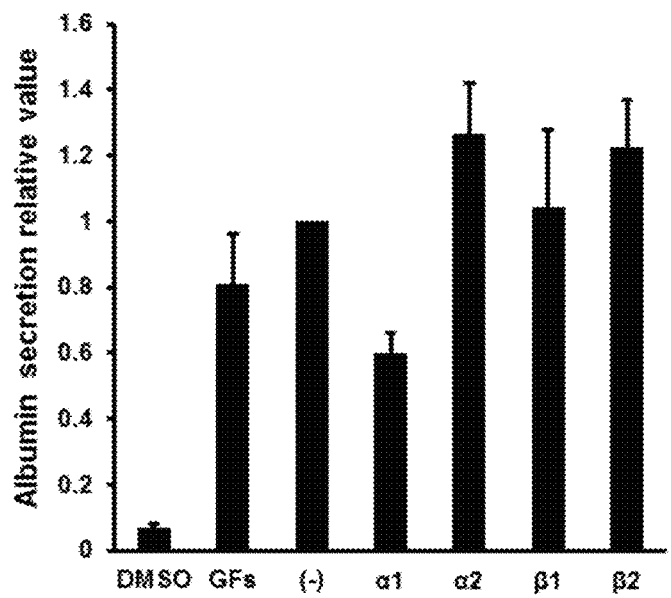
FIG. 15 shows albumin secretion volume in the cells induced by using various iPS cell lines in accordance with the method of the present invention. In the figure, DMSO shows the results of the differentiated cells induced by adding DMSO in Stage 3; GFs shows the results of the differentiated cells induced by adding HGF+oncostatin M in Stage 3; (−) shows the results of the differentiated cells induced by adding methoxamine alone in Stage 3; α1 shows the results of the differentiated cells induced by adding methoxamine and doxazosin in Stage 3; α2 shows the results of the differentiated cells induced by adding methoxamine and yohimbine in Stage 3; β1 shows the results of the differentiated cells induced by adding methoxamine and metoprolol in Stage 3; and β2 shows the results of the differentiated cells induced by adding methoxamine and butoxamine in Stage 3.

To study the mechanism of methoxamine to increase the efficacy of hepatocyte induction, adrenergic receptor blocking agents against each adrenergic receptor were added and the secretions of albumin from the resulting cells were measured. The period of Stage 1 of the aforementioned method was set to be 6 days (Stage 1-1: 1 day, Stage 1-2: 2 days and Stage 1-3: 3 days); the period of Stage 2 was set to be 6 days; and the period of Stage 3 was set to be 8 days. Methoxamine and each adrenergic receptor blocking agent were added in Stage 3. The adrenergic receptor blocking agents used herein were as follows: 10 µM doxazosin (Sigma) as an $\alpha 1$ blocking agent; 10 µM yohimbine (Sigma) as an $\alpha 2$ blocking agent; and 10 µM metoprolol (Sigma) as a $\beta 1$ blocking agent; and 10 µM butoxamine (Sigma) as a $\beta 2$ blocking agent. The volume of albumin secretion decreased when doxazosin was added in the presence of methoxamine (FIG. 15). Hence, it was suggested that the efficiency of hepatocyte induction from iPS cells can be increased by keeping at least adrenergic $\alpha 1$ receptor active.

Gene Expression Profile Analysis

Figure 16:
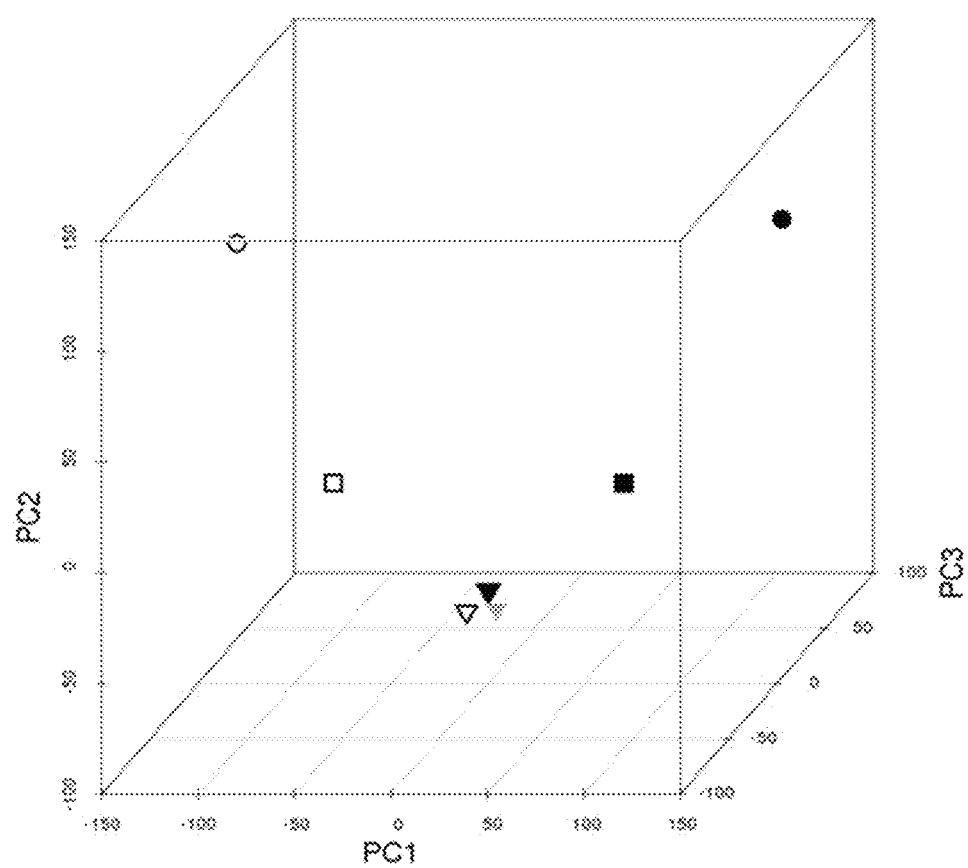
FIG. 16 shows principal component analysis (PCA), which is the results obtained by comparing gene expression profiles of hepatocytes obtained by differentiation induction from human iPS cells in accordance with RNA sequencing analysis.
Figure 17:
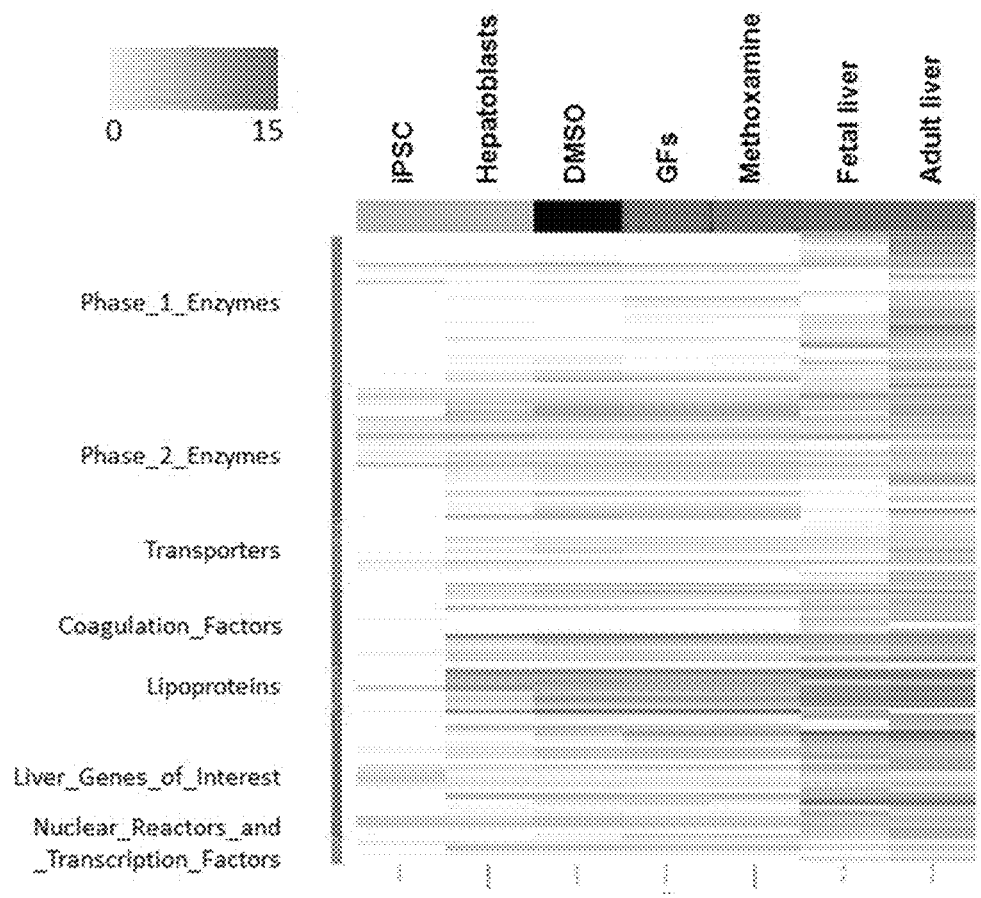
FIG. 17 shows the heat map of liver marker gene expression, which is the results obtained by comparing gene expression profiles in accordance with RNA sequencing analysis.
Figure 18:
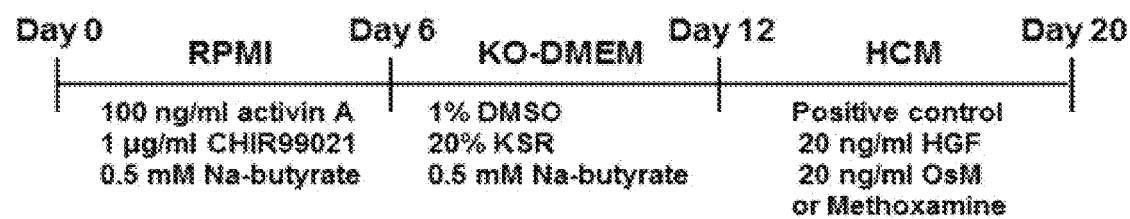
FIG. 18 schematically shows induction of hepatocytes from mouse ES cells.

The hepatocytes induced from human iPS cells were subjected to RNA sequencing analysis and gene expression profiles were compared. FIG. 16 shows principal component analysis (PCA) and FIG. 17 shows the heat map of liver marker gene expression. From these results, it was found that the hepatocytes induced by using growth factors (HGF and OsM) known in the art and hepatocytes induced by using methoxamine have substantially the same gene expression profile.

Example 6

Induction of Hepatocytes from ES Cells

<Stage 1>

Mouse ES cells (D3 cell line) were separated into single cells by adding 0.25% trypsin-EDTA (GIBCO). In order to remove feeder cells, the cells were seeded in a plate coated with gelatin. Ten to twenty minutes later, the supernatant containing the ES cells and the culture medium was collected, then the cells were seeded in a 24-well plate coated with Matrigel basement Membrance Matrix Growth Factor Reduced (BD) such that the cells were placed in a rate of $2.0 \times 10^4$-$8.0 \times 10^4$ cells/well. The cells were cultured in RPMI1640 supplemented with 1 µM CHIR99021 (Axon Medchem), 100 ng/ml Activin A (R&D systems), 2% B27 (Invitrogen) and 0.5% PenStrep (Invitrogen) for one day (Stage 1-1) (day 1).

Subsequently, 0.5 mM NaB (Sigma) was added to the medium and the cells were cultured for one day (Stage 1-2) (day 2). The medium was removed and the cells were cultured in RPMI1640 supplemented with 0.5 mM NaB (Sigma), 1 µM CHIR99021 (Axon Medchem), 100 ng/ml Activin A (R&D systems), 2% B27 (Invitrogen) and 0.5% PenStrep (Invitrogen) for 4 days (Stage 1-3) (day 6). The cells obtained in the above steps were stained with a Sox17 antibody. The content ratio of Sox17-positive cells was determined. A cell population containing 60% to 80% of Sox17-positive cells (endodermal cells) was obtained.

<Stage 2>

After completion of Stage 1, the medium was exchanged with Knockout™ DMEM (Invitrogen) supplemented with 1% DMSO, 20% KSR (Invitrogen), 1 mM L-glutamic acid, 1% NEAA (Invitrogen), 0.1 mM β mercaptoethanol, 0.5 mM NaB (Sigma) and 0.5% PenStrep. The cells were cultured for 6 days and the resultant cells were stained with an AFP antibody. The content ratio of AFP-positive cells was determined. A cell population containing 40% to 60% of AFP-positive cells (hepatoblasts) was obtained (day 12).

<Stage 3>

After completion of Stage 2, the medium was exchanged with the Hepatocyte Culture Medium (HCM SingleQuots Kit) (LONZA) supplemented with 1 µM pregnenolone (Tokyo Kasai), methoxamine hydrochloride (Sigma), etilefrine or phenylephrine. The cells were cultured for 8 days. At this time, as a control, cells were cultured in a Hepatocyte Culture Medium (HCM SingleQuots Kit) supplemented with 1% DMSO or 20 ng/ml HGF and 20 ng/ml oncostatin M in the same manner.

Evaluation of Induced Hepatocytes

Figure 19:
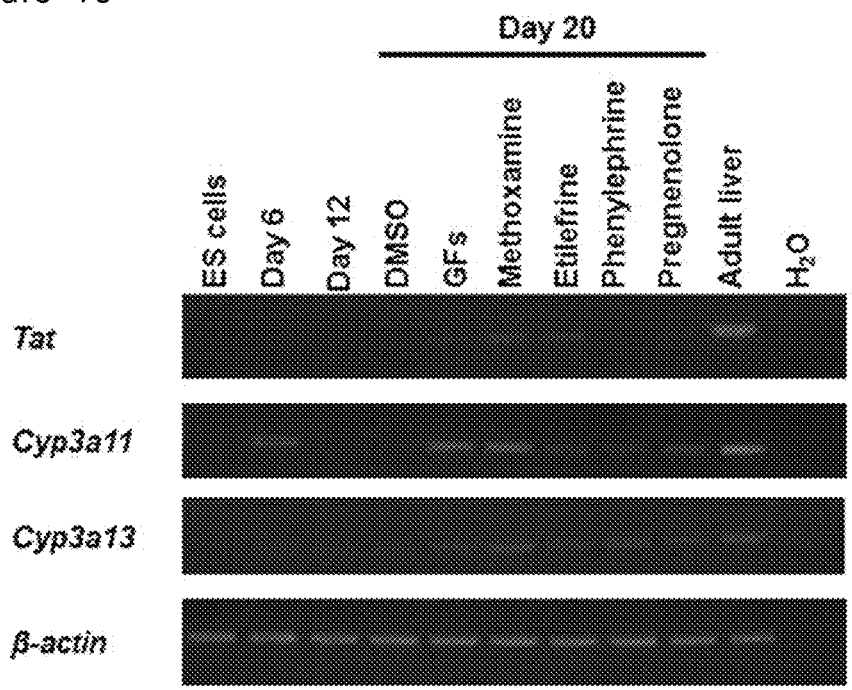
FIG. 19 shows expression of Tat, Cyp3a11, Cyp3a13 and β actin in the cells induced in different conditions.

In each of the undifferentiated cells (ES cells), cells on Day 6 (Stage 1 was completed), cells on Day 12 (at the time of completion of Stage 2), cells on Day 20 obtained by culturing the cells in the medium supplemented with HGF+ oncostatin M (GFs), methoxamine, etilefrine, phenylephrine, pregnenolone in Stage 3 for 8 days, and matured mouse hepatocytes, expression of tyrosine aminotransferase (Tat), drug metabolizing enzymes (Cyp3a11 and Cyp3a13) and β actin were measured. The result are shown in FIG. 19.

It was found that, in Stage 3, cell populations induced by adding pregnenolone, and adrenergic agonists, i.e., methoxamine, etilefrine and phenylephrine, express the same drug metabolizing enzymes as in the case where HGF+OsM was used.

Figure 20:
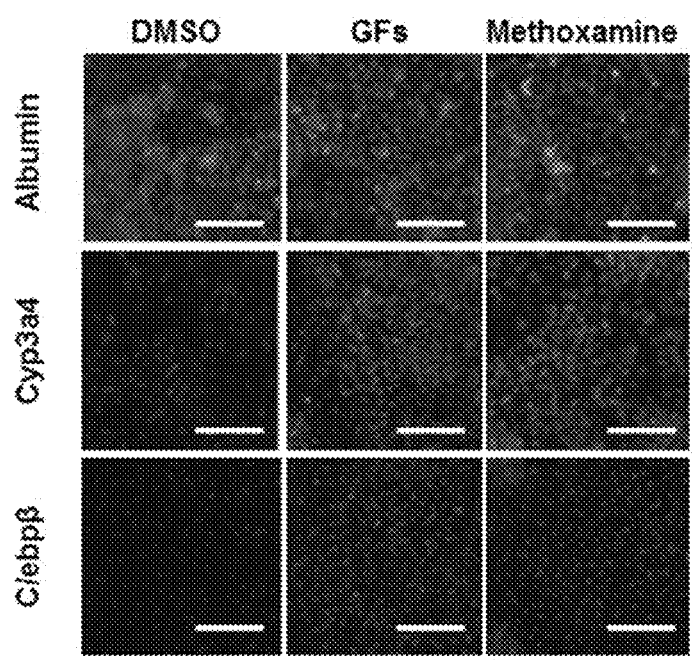
FIG. 20 shows images of cells induced by using agents (DMSO, HGF+oncostatin M (GFs), methoxamine) in Stage 3 and immunostained with an anti-albumin antibody, an anti-Cyp3a4 antibody and an anti-C/ebpβ antibody.

The cells cultured in the medium containing methoxamine in Stage 3 for 8 days, the cells cultured in the medium containing HGF+OsM (positive control) in the same manner as above and also the cells cultured in the medium containing DMSO (negative control) were used. These cells were immuno-stained with an anti-albumin antibody (Albumin), anti-Cyp3a4 antibody and anti-C/ebpβ antibody. The results are shown in FIG. 20. In each of the cases, very similar expression was observed in a cell group using the medium supplemented with HGF+OsM and a cell group using the medium supplemented with methoxamine.

INDUSTRIAL APPLICABILITY

As specifically described in the above, the present invention provides a method for inducing differentiation of pluripotent stem cells into hepatocytes. Owing to the method, the hepatocytes produced by the method of the invention can be used in regenerative medicine for treating liver diseases such as liver failure, safety tests for pharmaceuticals and drug metabolism tests.

What is claimed is:

1. A method for producing hepatocytes from pluripotent stem cells, comprising the following steps (i) to (iii):
   (i) culturing pluripotent stem cells in a medium containing Activin A and a GSK-3β inhibitor,
   (ii) culturing the cells obtained in step (i) in a medium containing DMSO, and
   (iii) culturing the cells obtained in step (ii) in a medium for culturing hepatocytes containing pregnenolone; wherein said step produces hepatocytes.

2. The method according to claim 1, wherein step (i) further includes culturing the cells in a medium containing Activin A, a GSK-3β inhibitor and an HDAC inhibitor.

3. The method according to claim 2, wherein the GSK3β inhibitor is CHIR99021 and the HDAC inhibitor is sodium butyrate (NaB).

4. The method according to claim 1, wherein the pluripotent stem cells are iPS cells.

5. The method according to claim 4, wherein the iPS cells are human iPS cells.

6. The method according to claim 1, wherein the pluripotent stem cells are ES cells.

7. The method according to claim 1, wherein the concentration of pregnenolone in the medium is 0.01 μM to 10 μM.

8. The method according to claim 1, wherein the concentration of pregnenolone in the medium is 0.05 μM to 5 μM.

9. The method according to claim 1, wherein the concentration of pregnenolone in the medium is 0.1 μM to 2.5 μM.

* * * * *